(12) United States Patent
Madiyalakan et al.

(10) Patent No.: US 7,361,346 B1
(45) Date of Patent: *Apr. 22, 2008

(54) THERAPEUTIC COMPOSITIONS THAT PRODUCE AN IMMUNE RESPONSE

(75) Inventors: Ragupathy Madiyalakan, Edmonton (CA); Antoine A. Noujaim, Edmonton (CA); Richard P. Baum, Frankfurt (DE); Birgit Schultes, Edmonton (CA); Beatrice Leveugle, Edmonton (CA); Fernando Kreutz, Rio Grande do Sul (BR)

(73) Assignee: Altarex Corp., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/152,698

(22) Filed: Sep. 2, 1998

Related U.S. Application Data

(63) Continuation-in-part of application No. 08/913,290, filed as application No. PCT/IB96/00461 on May 15, 1996, now Pat. No. 6,241,985, and a continuation-in-part of application No. 08/877,511, filed on Jun. 17, 1997, now Pat. No. 6,086,873, which is a continuation-in-part of application No. PCT/IB96/00461, application No. 09/152,698, which is a continuation-in-part of application No. 09/094,598, filed on Jun. 15, 1998, now abandoned, which is a continuation-in-part of application No. 08/877,511, and a continuation-in-part of application No. PCT/IB96/00461.

(51) Int. Cl.
*A61K 39/00* (2006.01)
*A61K 39/385* (2006.01)

(52) U.S. Cl. .................. 424/178.1; 424/193.1; 424/277.1

(58) Field of Classification Search .......... 424/184.1, 424/174.1, 178.1, 193.1; 530/388.8, 388.85
See application file for complete search history.

(56) References Cited

U.S. PATENT DOCUMENTS

| | | | |
|---|---|---|---|
| 4,740,371 A | * | 4/1988 | St.Remy et al. |
| 4,879,225 A | * | 11/1989 | Morgan, Jr. et al. |
| 5,053,224 A | * | 10/1991 | Koprowski et al. |
| 5,240,833 A | | 8/1993 | Nudelman |
| 5,512,283 A | * | 4/1996 | Byers et al. |
| 5,583,202 A | * | 12/1996 | Zanetti et al. |
| 5,591,593 A | * | 1/1997 | Courtenay-Luck |
| 5,652,114 A | * | 7/1997 | Chu et al. |
| 5,688,657 A | * | 11/1997 | Tsang et al. |
| 5,725,856 A | | 3/1998 | Hudziak et al. |
| 5,807,978 A | | 9/1998 | Kokolus |
| 5,869,445 A | * | 2/1999 | Cheever et al. |
| 5,976,818 A | * | 11/1999 | O'Brien ............ 435/7.23 |
| 6,068,830 A | * | 5/2000 | Diamandis et al. |
| 6,077,519 A | * | 6/2000 | Storkus et al. |
| 6,088,613 A | | 7/2000 | Unger |
| 6,096,289 A | | 8/2000 | Goldenberg |
| 6,140,091 A | * | 10/2000 | Raso et al. |

FOREIGN PATENT DOCUMENTS

| | | |
|---|---|---|
| EP | 0 153 871 | 9/1985 |
| WO | WO 93/20185 | * 10/1993 |
| WO | WO 94/21287 | * 9/1994 |
| WO | WO95/04548 | 2/1995 |
| WO | WO98/57661 | 12/1998 |
| WO | WO 99/65517 | * 12/1999 |

OTHER PUBLICATIONS

Clark, Protein Engineering of antibody Molecules for Prophylactic and therapeutic Applications in Man, (monograph), 1993, p. 1.*
Chattopadhyay et al, Cancer Research, 1991, vol. 51, pp. 6045-6051.*
Rooijen, Res Immunol, 1993, vol. 144, pp. 545-552.*
Klaus, Nature, 1978, vol. 272, pp. 265-266.*
Tassi et al, Immunology Letters, 1991, vol. 27, pp. 39-44.*
Frodin et al, Hybridoma, 1991, vol. 10, pp. 421-431. (abstract).*
Fagerberg et al, Cancer Immunol Immunother, 1996, vol. 42, pp. 81-87. (abstract).*
Herbert, Dictionary of Immunology, p. 79.*
Schlom, In: Molecular foundations of Oncology, S. Broder, Ed., 1991, pp. 105-107.*
Baum et al (Cancer, 1994, vol. 73 (3 suppl), pp. 1121-1125).*
Wagner et al (Biotechnology Therapeutics, 1992, vol. 3, pp. 81-89).*
Schwartz, ("Cancer Markers", In: Cancer: Principles and Practice of Clinical Oncology, 4th Edition, 1994, DeVita et al, Ed.s., p. 531-542).*
Goldenberg et al ("Cancer Diagnosis and Therapy with Radiolabeled Antibodies", In: Immunoconjugates, Antibody Conjugates in Radioimaging and Therapy of Cancer, Vogel. Ed., 1987, pp. 259-280).*
The abstract of Bachmann et al (European Journal of Immunology, 1994, vol. 24, pp. 2567-2570).*
The abstract of Yin et al (International Journal of Cancer, 1996, vol. 65, pp. 406-412).*
The abstract of McGuckin et al (Clinica Chimica Acta, 1993, vol. 214, pp. 139-151).*
Kedar et al ('Cancer Immunotherapy' In: Advances in CanceR Research, 1992, vol. 59, pp. 245-323).*
Crowley et al (Journal of Experiemtnal Medicine, 1990, vol. 172, pp. 383-386).*
Sallusto et al (Journal of Experiemtnal Medicine, 1994, vol. 179, pp. 1109-1118.*
de La Salle et al ('FcgR on Humna Dendritic Cells' In:Human IgG Receptors, 1996, pp. 39-55, Van de winkel et al Eds).*

(Continued)

*Primary Examiner*—Karen A. Canella
(74) *Attorney, Agent, or Firm*—Ropes & Gray LLP

(57) ABSTRACT

The invention provides a method for stimulating the production of antibodies to a cryptic epitope on a soluble antigen by administering to a patient having such a cryptic epitope a binding agent that binds to the soluble antigen and forming a complex between the binding agent and the soluble antigen, wherein the cryptic epitope is exposed and the patient generates antibodies that bind to the cryptic epitope.

37 Claims, 19 Drawing Sheets

OTHER PUBLICATIONS

Dong et al (In: VAccine Desgin: The Subunit Approach, Powell et al, Ed., 1995, pp. 625-643).*
Vrba et al (PNAS, 1975, vol. 72, pp. 4602-4606).*
Paul (Fundamental Immunology, (text), 1993, p. 1163).*
The abstract of Jurncic-Winkler et al (Eur Urol, 1993, vol. 24, pp. 487-491).*
Simitsek et al (J Exp Med, 1995, vol. 181, pp. 1957-1963).*
Nishimura et al, Cancer Chemother Pharmacol, 2000, vol. 46, suppl. pp. S52-S61.*
Watts et al, J Exp Med, 1993, vol. 178, pp. 1495-1463.*
Cibotti et al PNAS, 1992, vol. 89, pp. 416-420.*
Abstract of Pani et al (Immunological Investigations, 1994, vol. 23, pp. 337-346).*
Benichou et al, 1994, vol. 6, pp. 131-138.*
Lee et al, Journal of Immunology, 1999, vol. 163, pp. 6292-6300).*
Ohlen et al (Journal of Immunology, 2001, vol. 166, pp. 2863-2870).*
Antonia et al (International Immunology, 1995, vol. 7, pp. 715-725).*
Paul, Fundamental Immunology, (text), 1993, pp. 1163-1169.*
Abstract of Semino et al (Journal of Biological Regulators and Homeostatic Agents, 1993, vol. 7, pp. 99-105.*
Abstract of Algarra et al, International Journal of Clinical and Laboratory Research, 1997, vol. 27, pp. 95-102.*
Bodey et al (Anticancer Research, Jul.-Aug. 2000, vol. 20, pp. 2665-2676.*
PCT International Search Report Corresponding To PCT International Application No. PCT/IB99/01114; Authorized Officer: M. Covone: Date of Completion: Nov. 30, 1999; Date of Mailing: Dec. 15, 1999 (8 pages).
Madiyalakan, R. et al., HYBRIDOMA, vol. 14, No. 2, 1995, "Antiidotype Induction Therapy: Evidence for the induction of Immune Response through the Idiotype Network in Patients with Ovarian Cancer after Administration of Anti-CA125 Murine Monoclonal Antibody B43.13", pp. 199-203.
Leveugle, B. et al., Proceedings of the American Associate for Cancer Research Annual Meeting, vol. 39, Mar. 1998, "PSA-directed immunotherapy of prostate cancer.", p. 355, (1 page).

Foon, K.A. et al., Clinical Cancer Research, vol. 3, Aug. 1997, "Clinical and Immune Responses in Advanced Colorectal Cancer Patients Treated with Anti-Idiotype Monoclonal Antibody Vaccine That Mimics the Carcinoembryonic Antigen", pp. 1267-1276.
Uemura, H. et al., Jpn J. Cancer Res., vol. 7, No. 10, 1995, "Generation of anti-idiotype antibodies related to prostatic specific antigen" (meeting abstract), p. 427.
Schultes, B.C. et al., Cancer Immunol Immunother, vol. 46, No. 4, Jun. 1998, "Anti-idiotype induction therapy: anti-CA125 antibodies ($Ab_3$) mediated tumor killing in patients treated with Ovarex mAb B43.13 ($Ab_1$)", pp. 201-212.
Baum, 1994, Activating Anti-Idiotypic Human Anti-Mouse Antobodies for Immunotherapy of Ovarian Carcinoma, Cancer 73:1121-1125.
Golumbek et al., 1993, The Antitumor Immune-Response as a Problem of Self-NonSelf Discrimination—Implications for Immunotherapy, Immunologic Res. 12:183-192 (Abstract only).
Jacobs and Haskell, 1991, Clinical Use of Tumor Markers in Oncology, Curr. Probl Cancer 15(6):299-360.
Lanzavecchia, 1996, Mechanisms of antigen uptake for presentation, Curr. Opin. Imm. 8:348-354.
Leitzel et al., 1992, Elevated Soluble c-erbB-2 Antigen Levels in the Serum and Effusions of a Proportion of Breast Cancer Patients, J. Clin. Oncol. 10(9):1436-1443.
Madiyalakan et al., 1997, OVAREX™ Mab-B43.13:IFN-y Could Improve the Ovarian Tumor Cell Sensitivity to CA125-Specific Allogenic Cytotoxic T Cells, Hybridoma 16:41-45.
Wagner et al., 1992, Immunotherapy of Advanced Ovarian Carcinomas by Activation of the Idiotypic Network, Biotech. Ther. 3:81-89.
Ward et al., 1997, Unconjugated antibodies for cancer therapy: lessons from the clinic, Cancer Treatment Rev. 23:305-319.
Schultze et al., "DCs and CD40-activated B cells: current and future avenues to cellular cancer immunotherapy." Trends in Immunology 25:659-664, (2004).

* cited by examiner

| | | | | | | | | | |
|---|---|---|---|---|---|---|---|---|---|
| E 139 | E 140 | | | | | | | | |
| F 141 | L 142 | T 143 | P 144 | K 145 | K 146 | L 147 | Q 148 | C 149 | V 150 |
| D 151 | L 152 | H 153 | V 154 | I 155 | S 156 | N 157 | D 158 | V 159 | C 160 |
| A 161 | Q 162 | V 163 | | | | | | | |

THERAPEUTIC COMPOSITIONS THAT PRODUCE AN IMMUNE RESPONSE

This application is a continuation-in-part of U.S. Ser. No. 08/913,290, a U.S. national stage application of International Application No. PCT/IB96/00461, filed under 35 U.S.C. § 371 on May 15, 1996, now U.S. Pat. No. 6,241,985; a continuation-in-part of U.S. Ser. No. 08/877,511, filed Jun. 17, 1997, now U.S. Pat. No. 6,086,873, which is a continuation-in-part of International Application No. PCT/IB96/00461, filed May 15, 1996, now WO 97/42973 A1; and a continuation-in-part of U.S. Ser. No. 09/094,598, filed Jun. 15, 1998, now abandoned, which is a continuation-in-part of U.S. Ser. No. 08/877,511, filed Jun. 17, 1997, now U.S. Pat. No. 6,086,873, which is a continuation-in-part of International Application No. PCT/IB96/00461, filed May 15, 1996, now WO 97/42973 A1. U.S. Ser. No. 09/094,598 is also a continuation-in-part of PCT/IB96/00461.

TECHNICAL FIELD

The invention concerns methods and compositions having increased therapeutic effect by altering the immunogenicity of the active component without decreasing the active component's antigenicity. For some embodiments of the invention, e.g., cancer immunotherapy, immunogenicity is increased. The invention also concerns methods and compositions for stimulating a host's immune response, particularly for the treatment of cancer. The methods and compositions according to the invention use binding agents such as antibodies to generate an immune response to a pre-determined antigen.

BACKGROUND ART

In vertebrates, the mechanisms of natural and specific immunity cooperate within a system of host defenses, the immune system, to eliminate foreign invaders. In addition to microbes, cancer cells, parasites and virus-infected cells, the immune system also recognizes and eliminates cells or tissues transplanted into a subject from a genetically different individual of the same species (allografts) or from a different species (xenografts).

Treatment for cancer has traditionally encompassed three main strategies: surgery, chemotherapy, and radiotherapy. Although considerable progress in these areas has been attained, the search for more effective and safe alternative treatments continues.

The hypothesis that the immune system ought to be able to recognize tumors and thus could be recruited in the fight against cancer has been a driving force behind outstanding efforts of many immunologists. This approach is attractive because of the unique ability of the immune system to specifically destroy affected cells while mostly sparing normal tissue. Moreover, the initial immune response is known to leave behind a long-term memory that serves to protect from the same disease in the future. No drug treatment for cancer can claim such specificity or memory.

An immunotherapeutic strategy for the treatment of cancer and other diseases involve one or more components of the immune system to trigger a complex cascade of biological reactions focused on eliminating a foreign molecule from the host. Vertebrates have two broad classes of immune responses: antibody responses, or humoral immunity, and cell-mediated immune responses, or cellular immunity.

Humoral Immunity

Humoral immunity is provided by B lymphocytes, which, after proliferation and differentiation, produce antibodies (proteins also known as immunoglobulins) that circulate in the blood and lymphatic fluid. These antibodies specifically bind to the antigen that induced them. Binding by antibody inactivates the foreign substance, e.g., a virus, by blocking the substance's ability to bind to receptors on a target cell or by attracting complement or the killer cells that attack the virus. The humoral response primarily defends against the extracellular phases of bacterial and viral infections. In humoral immunity, serum alone can transfer the response, and the effectors of the response are protein molecules, typically soluble, called antibodies. Lymphocytes determine the specificity of immunity, and it is their response that orchestrates the effector limbs of the immune system. Cells and proteins, such as antibodies, that interact with lymphocytes play critical roles in both the presentation of antigen and in the mediation of immunologic functions.

Individual lymphocytes respond to a limited set of structurally related antigens. As noted in more detail below, this function is defined structurally by the presence of receptors on the lymphocyte's surface membrane that are specific for binding sites (determinants or epitopes) on the antigen.

Lymphocytes differ from each other not only in the specificity of their receptors, but also in their functions. One class of lymphocytes, B cells, are precursors of antibody-secreting cells, and function as mediators of the humoral immune response. Another class of lymphocytes, T cells, express important regulatory functions, and are mediators of the cellular immune response.

Cellular Immunity

The second class of immune responses, cellular immunity, involve the production of specialized cells, e.g., T lymphocytes, that react with foreign antigens on the surface of other host cells. The cellular immune response is particularly effective against fungi, parasites, intracellular viral infections, cancer cells and other foreign matter. In fact, the majority of T lymphocytes play a regulatory role in immunity, acting either to enhance or suppress the responses of other white blood cells. These cells, called helper T cells and suppressor T cells, respectively, are collectively referred to as regulatory cells. Other T lymphocytes, called cytotoxic T cells, kill virus-infected cells. Both cytotoxic T cells and B lymphocytes are involved directly in defense against infection and are collectively referred to as effector cells.

The time course of an immune response is subdivided into the cognitive or recognition phase, during which specific lymphocytes recognize the foreign antigen; the activation phase, during which specific lymphocytes respond to the foreign antigen; and the effector phase, during which antigen-activated lymphocytes mediate the processes required to eliminate the antigen. Lymphocytes are immune cells that are specialized in mediating and directing specific immune responses. T cells and B cells become morphologically distinguishable only after they have been stimulated by an antigen.

In addition to a humoral response, the immune system may also generate a cellular response mediated by activated T-cells. There are a number of intercellular signals important to T cell activation. Under normal circumstances an antigen degrades or is cleaved to form antigen fragments or peptides. Presentation of antigen fragments to T-cells is the principal function of MHC molecules, and the cells that carry out this function are called antigen-presenting cells (APC: including but not limited to dendritic cells, macrophages, and B cells).

The capture and processing of an antigen by APCs is essential for the induction of a specific immune response. The three major APCs are dendritic cells, macrophages and B-lymphocytes; dendritic cells are the most efficient. The injected antibody can form a complex with a circulating antigen (e.g., PSA or Ca 125), these immune complexes can be targeted to dendritic cells and macrophages through the Fc-receptors present on these cells. However the high number of Fc receptors on neutrophils may considerably limit this process.

Cancer immunotherapy is based on the principle of inducing or activating the immune system to recognize and eliminate neoplastic cells. The key elements in any immunotherapy is to induce or trigger the host immune system to first recognize a molecule as an unwanted target, and then to induce the system to initiate a response against that molecule. In healthy hosts, the immune system recognizes surface features of a molecule that is not a normal constituent of the host (i.e., is "foreign" to the host). Once the recognition function occurs, the host must then direct a response against that particular foreign molecule.

Both the recognition and the response elements of the immune system involve a highly complex cascade of biological reactions. In most immunologically based disorders, at least one of the steps in the recognition phase, or at least one of the steps in the response phase, are disrupted. Virtually any disruption in either of these complex pathways leads to a reduced response or to the lack of any response. The inability of the immune system to destroy a growing tumor has been attributed, among other factors, to the presence of tumor-associated antigens (TAA) that induce immunological tolerance and/or immunosuppression. For example, in some kinds of cancer, the cancer itself tricks the host into accepting the foreign cancer cell as a normal constituent, thus disrupting the recognition phase of the immune system. The immunological approach to cancer therapy involves modification of the host-tumor relationship so that the immune system is induced or amplifies its response to the TAAs. If successful, inducing or amplifying the immune system can lead to tumor regression, tumor rejection, and occasionally, to tumor cure.

Antigenicity and Immunogenicity

As used herein, if a binding agent can be recognized by an antigen, i.e., can bind to or interact with an antigen, then the binding agent is said to be antigenic. If the immune system can also mount an active response against the binding agent, a complex containing the binding agent, a portion of the complex, or the antigen, it is said to be immunogenic.

The conventional definition of an antigen is a substance that can elicit in a vertebrate host the formation of a specific antibody or the generation of a specific population of lymphocytes reactive with the substance. As frequently occurs in science, however, it is now known that this definition, although accurate, is not complete. For example, it is now known that some disease conditions suppress or inactivate the host immune response, and the substance that would have been expected to elicit an antibody or generate specific lymphocytes, does not. Thus, not all antigens are capable of eliciting a human immune response.

Typically, the antibody's capability of binding the antigen is based on highly complementary structures. That is, the shape of the antibody must contain structures that are the compliment of the structures on the antigen. The portion of the antigen to which an antibody binds is called the "antigenic determinant", or "epitope". Thus antigens are molecules that bear one or more epitopes which may be recognized by specific receptors in an immune system, a property called antigenicity.

Antigens are molecules that interact with specific lymphocyte receptors—surface T cell antigen receptors and B cell immunoglobulin receptors. A particular B or T cell binds to a very specific region of the antigen, called an antigenic determinant or epitope.

Immunogenicity refers to the property of stimulating the immune system to generate a specific response. Thus, all immunogens are antigens, but not vice-versa. Although an immune system may recognize an antigen (e.g., binds to a T or B cell receptor), it does not respond to the antigen unless the antigen or an antigen-containing complex is also immunogenic.

An immune response to a particular antigen is greatly influenced by the structure and activity of the antigen itself, as well as myriad other factors. In some cases, the immune system is not able to generate an immune response to a particular antigen, a condition that is called tolerance.

In influencing whether an antigen is immunogenic or immunotolerant, an important characteristic of the antigen is the degree of difference between the antigen and similar molecules within the host. The most immunogenic antigens are those that have no homologs in the host, i.e., those that are most "foreign." Other factors that promote immunogenicity include higher molecular weight, greater molecular complexity, the proper antigen dose range, the route of administration, the age of the host, and the genetic composition of the host (including exposure to antigens during fetal development).

As noted above, antigens may have one or more epitopes or binding sites that are recognized by specific receptors of the immune system. Epitopes may be formed by the primary structure of a molecule (called a sequential epitope), or may be formed by portions of the molecule separate from the primary structure that juxtapose in the secondary or tertiary structure of the molecule (called a conformational epitope). Some epitopes are hidden in the three dimensional structure of the native antigen, and become immunogenic only after a conformational change in the antigen provides access to the epitope by the specific receptors of the immune system. Some antigens, e.g., tumor-associated antigens such as ovarian cancer or breast cancer antigens, have multiple antibody binding sites. These antigens are termed "multi-epitopic" antigens.

An important feature and function of a comprehensive therapeutic reagent is the ability to initiate recognition and response to an antigen, to induce a cellular and humoral response (either or both) to the antigen, and to increase the immunogenicity of a mole without affecting its antigenicity.

To cope with the immense variety of epitopes encountered, the immune system of a mammalian individual contains an extremely large repertoire of lymphocytes, approximately $2 \times 10^{12}$. Each lymphocyte clone of the repertoire contains surface receptors specific for one epitope. It is estimated that the mammalian immune system can distinguish at least $10^8$ distinct antigenic determinants. Even a single antigenic determinant will, in general, activate many clones, each of which produces an antigen-binding site with its own characteristic affinity for the determinant.

Antibodies, also known as immunoglobulins, are proteins. They have two principal functions. The first is to recognize (bind) antigens. The second is to mobilize other elements of the immune system to destroy the foreign entity. An antibody binds to an epitope of an antigen as a result of molecular complementarity. The portions of the antibody which participate directly in the interaction is called "antigen binding site", or "paratope". The antigens bound by a particular antibody are called its "cognate antigens".

Antibodies bear three major categories of antigen-specific determinants—isotypic, allotypic, and idiotypic—each of which is defined by its location on the antibody molecule. For the purpose of the present invention, we shall only focus on the idiotypic category.

Idiotypic determinants, or idiotopes, are markers for the V region of an antibody, a relatively large region that may include several idiotopes each capable of interacting with a different antibody. The set of idiotopes expressed on a single antibody V region constitutes the antibody idiotype. An antibody (Ab1) whose antigen combining site (paratope) interacts with an antigenic determinant on another antibody V region (idiotope) is called an anti-idiotypic antibody (Ab2). Thus, an Ab2 antibody includes an antigen binding site, and may include one or more antibody binding sites.

The idiotype of an antibody is defined by individually distinctive antigenic determinants in the variable or idiotypic region of the antibody molecule. A portion of these idiotypic determinants will be on or closely associated with the paratope of the antibody, while others will be in the framework of the variable region. While each antibody has its own idiotype, particular antibodies will be referred to below by the following terms. "Idiotype antibody" or "Id Ab" refers to an anti-antibody (i.e., the epitope identified by the idiotype antibody is on a cell or a soluble antigen, such as a tumor associated antigen). "Anti-idiotype antibody" or "anti-Id Ab" refers to an antibody which identifies an epitope in the variable region of an idiotype antibody. A portion of such antibodies will identify an epitope within the paratope of the idiotype antibody, thus presenting an "internal" image of the epitope identified by the idiotype antibody on the tumor associated antigen. "Anti-(anti-idiotype) antibody" or "anti-(anti-Id) Ab" is an antibody that identifies an epitope in the variable region of the anti-idiotype antibodies. A portion of the anti-(anti-idiotype) antibodies will identify an epitope that corresponds to (i) the paratope of the anti-idiotype antibody, and (ii) an epitope on a tumor associated antigen.

There are four types of anti-idiotypic antibodies, sometimes called Ab2α, Ab2β, Ab2γ, and Ab2δ. In one type of anti-idiotype antibody (Ab2β), the combining site perfectly mimics the structure of the antigen epitope recognized by the Ab1 antibody (i.e., whose paratope always mimics the epitope of the original antigen). This type of anti-idiotype is said to represent the internal image of the antigen. By definition, the antigen and this type of anti-idiotype antibody compete for the same binding site on Ab1, and the antigen inhibits the interaction between Ab1 and the anti-idiotypic antibody. The phenomenon of producing an anti-idiotypic antibody having the internal image of the antigen may permit the use of antibodies to replace the antigen as an immunogen.

The second type of anti-idiotype, Ab2α, binds an epitope remote from the paratope of the primary antibody (binds to an idiotope of Ab1 that is distinct from the antigen binding site), and therefore may be characterized in terms of the antigen's inability to prevent the binding of the anti-idiotype to Ab1. For this type of anti-idiotype, Ab1 can bind to both the antigen and the anti-idiotypic antibody. For a graphic representation of these types of antibodies and their interaction, see FIG. 1.

The third type, Ab2γ, binds near enough to the paratope of the primary antibody to interfere with antigen binding. The fourth type, Ab2δ, recognizes an idiotypic determinant that mimics a constant domain antigenic structure.

Anti-idiotypic antibodies often have immunological characteristics similar to those of an antigen cognate to the immunizing antibody. Anti-isotypic antibodies, on the other hand, bind epitopes in the constant region of the immunizing antigen.

For tumors that have antigens, there are at least four theories why the immune response may fail to destroy a tumor: 1) there are no B cells or cytotoxic T lymphocytes (CTL) capable of recognizing the tumor; 2) there are no TH cells capable of recognizing the tumor; 3) TS cells become activated before TH cells, thus preventing B-cell and CTL activation; and 4) the genes regulating tumor proliferation may be present from birth, so the host does not treat the gene products as "foreign."

"Passive immunotherapy" involves the administration of antibodies to a patient. Antibody therapy is conventionally characterized as passive since the patient is not the source of the antibodies. However, the term passive is misleading because the patient can produce anti-idiotypic secondary antibodies which in turn can provoke an immune response which is cross-reactive with the original antigen. "Active immunotherapy" is the administration of an antigen, in the form of a vaccine, to a patient, so as to elicit a protective immune response. Genetically modified tumor cell vaccines transfected with genes expressing cytokines and co-stimulatory molecules have also been used to alleviate the inadequacy of the tumor specific immune response.

If a specific antibody from one animal is injected as an immunogen into a suitable second animal, the injected antibody will elicit an immune response (e.g., produce antibodies against the injected antibodies—"anti-antibodies"). Some of these anti-antibodies will be specific for the unique epitopes (idiotopes) of the variable domain of the injected antibodies. These epitopes are known collectively as the idiotype of the primary antibody; the secondary (antibodies which bind to these epitopes are known as anti-idiotypic antibodies. The sum of all idiotopes present on the variable portion of an antibody is referred to as its idiotype. Idiotypes are serologically defined, since injection of a primary antibody that binds an epitope of the antigen may induce the production of anti-idiotypic antibodies. When binding between the primary antibody and an anti-idiotypic antibody is inhibited by the antigen to which the primary antibody is directed, the idiotype is binding site or epitope related. Other secondary antibodies will be specific for the epitopes of the constant domains of the injected antibodies and hence are known as anti-isotypic antibodies. As used herein, anti-idiotypic antibody, epitope, or epitopic are used in their art-recognized sense.

The various interactions based on idiotypic determinants, called the idiotypic network, is based on the immunogenicity of the variable regions of immunoglobulin molecules (Ab1) which stimulate the immune system to generate anti-idiotypic antibodies (Ab2), some of which mimic antigenic epitopes ("internal image") of the original antigen. The presence of internal image antibodies (Ab2) in the circulation can in turn induce the production of anti-anti-idiotypic antibodies (Ab3), some of which include structures that react with the original antigen.

The "network" theory states that antibodies produced initially during an immune response will carry unique new epitopes to which the organism is not tolerant, and therefore will elicit production of secondary antibodies (Ab2) directed against the idiotypes of the primary antibodies (Ab1). These secondary antibodies likewise will have an idiotype which will induce production of tertiary antibodies (Ab3) and so forth.

The network theory suggests that some of these secondary antibodies (Ab2) will have a binding site that is the complement of the original antigen and thus will reproduce the "internal image" of the original antigen. In other words, an anti-idiotypic antibody may be a surrogate antigen.

Two therapeutic applications arose from the network theory: 1) administer Ab1 which acts as an antigen inducing Ab2 production by the host; and 2) administer Ab2 which functionally imitates the tumor antigen.

The development of the "network" theory led investigators to suggest the direct administration of exogenously produced anti-idiotype antibodies, that is, antibodies raised against the idiotype of an anti-tumor antibody. Such an approach is disclosed in U.S. Pat. No. 5,053,224 (Koprowski, et al.) Koprowski assumes that the patient's body will produce anti-antibodies that will not only recognize these anti-idiotype antibodies, but also the original tumor epitope.

Conventional anti-idiotype antibodies are made by intraspecies or interspecies immunization with a purified antigen-specific pool of antibodies or a monoclonal antibody. The resulting antiserum is then extensively absorbed against similar molecules with the same constant region to remove antibodies with anti-$C_H C_L$ specificities. See, for example, Briles, et al.; "Idiotypic Antibodies," *Immunochemical Techniques* (New York, Academic; Colowich and Kaplan, eds; 1985). The production of anti-ID antibodies against self-idiotopes was one of the first key predictions of the network theory [Rodkey, S., *J. Exp. Med* 130:712-719 (1974)].

A human anti-idiotypic monoclonal antibody (Ab2) has been shown to induce anti-tumor cellular responses in animals and appears to prolong survival in patients with metastatic colorectal cancer. See Durrant, L. G. et al., "Enhanced Cell-Mediated Tumor Killing in Patients Immunized with Human Monoclonal Anti-Idiotypic Antibody 105AD7," *Cancer Research,* 54:4837-4840 (1994). The use of anti-idiotypic antibodies (Ab2) for immunotherapy of cancer is also reviewed by Bhattacharya-Chatterje, et al; *Cancer Immunol. Immunother.* 38:75-82 (1994).

Idiotopes on lymphoid receptors may in some cases mimic external antigens because of the extensive diversity of the immune system. This idea prompted many attempts to use the internal image of a foreign antigen, mimicked by the idiotypes of T or B receptors, to act as targets for anti-idiotypic antibodies. In this way, it has been proposed that anti-idiotypic antibodies may induce populations of T or B cells that can bind the extrinsic (or soluble) antigen. Such anti-idiotypic antibodies can be used as vaccines, many of which are summarized in Greenspan, N S, and Bona, C A; *The FASEB Journal,* 7:437-444 (1992).

The ability to up- or down-regulate immune responses and to control potentially auto-reactive immunocompetent cells is vital for normal immune function and survival. Regulatory mechanisms include the induction of clonal anergy (via inappropriate antigen-presenting cells), peripheral clonal deletion/apoptosis, cytokine (e.g. transforming growth factor-beta (TGF-β) or IL-10)-induced non-responsiveness, 'veto' cells, auto-reactive cytolytic T cells, and both non-specific and antigen-specific T suppressor cells. At least in theory, each of these regulatory systems provides a mechanistic basis for 'therapeutic intervention'.

In addition to cancer immunotherapy, control of abnormal acute and chronic inflammatory response is also one of the most important challenges in medicine. Typical examples of acute and chronic inflammation include atopy, urticaria, asthma, autoimmune hemolytic anemia, rheumatoid arthritis, systemic lupus erythematosus, granulomatous diseases, tuberculosis, and leprosy.

Like the tumor immune response described above, the aim of the inflammatory response is the elimination of harmful agents. Further, the treatment of autoimmune inflammatory disease is sometimes complicated by autoimmune factors that prevent the host from eliminating the harmful agents, thereby leading to a persistent or chronic inflammatory response or condition.

Presently, it has been determined that essential events in the development of inflammation includes a cellular response involving neutrophils and macrophages, specifically the rolling, activation, and adhesion of neutrophils to endothelium via selectins-carbohydrate ligand interaction (and may include neutrophil extravasation).

Therapeutic compositions for the treatment of inflammation have included agents that bind to one or more of the mediators of inflammation. For example, antibodies specific for selectin carbohydrate ligands, and inhibiting selectin-carbohydrate ligand binding, may be important anti-inflammatory targets for the development of therapeutic compositions for the treatment of inflammation.

In addition to the above, there are other cases where an anti-idiotypic mode of induction of a response may be useful. If a given epitope of a protein is discontinuous and results from three-dimensional folding, an anti-Id can be produced that would mimic that structure. Further, in immunizing against latent and/or immunosuppressive viruses, there is the possibility of well known deleterious effects not solvable by the use of attenuated viruses (e.g., mumps, measles, rubella, and HIV). The use of anti-ID induction of protective immunity may avoid these deleterious effects.

SUMMARY OF THE INVENTION

The present invention is a method and composition for generating both a humoral and/or a cellular immune response by administering a binding agent that specifically binds to a pre-selected soluble antigen. In accordance with the invention, the binding agent alone and/or the binding agent-soluble antigen complex, either acting as an immunogen, alters the immunogenic condition of the host. The binding agent or the binding agent/antigen complex generate new immunogens that are recognizable by the immune system. This leads to a humoral and/or a cellular response, which may include an anti-tumor response and/or cell killing.

The present invention is a comprehensive method for the treatment of certain diseases and conditions that includes, but is not limited to, targeting a soluble antigen, preferably a multi-epitopic antigen; and administering a binding agent, preferably a monoclonal antibody. In a preferred embodiment of the invention, the binding agent or the binding agent/antigen complex induces the production of a humoral response, as evidenced in part by the production of anti-tumor or anti-inflammation antibodies, Ab3 and/or Ab3'; and induces the production of a cellular response, as evidenced in part by the production of T-cells that are specific for the binding agent, the binding agent/antigen complex, and/or the antigen.

The present invention also includes methods and compositions for altering the immunogenic state of the host organism. In altering the immunogenic state, the compositions and methods of the present invention decrease, increase, or maintain the host's immunogenic state. In a most preferred embodiment of the invention, the methods and compositions do not decrease the antigenicity of the active component in the therapeutic composition. The present invention is preferably a method for increasing the over-all host response to a disease or condition.

The present invention also is a therapeutic composition comprising an active agent, or binding agent, that specifically binds to a pre-determined soluble antigen, wherein the binding agent, upon binding to the soluble antigen, forms a complex that is both antigenic and immunogenic.

The compositions and methods of the present invention may also include one or more steps or substances that increase the over-all immunogenicity.

The therapeutic compositions and methods of the present invention are suitable for the treatment of any disease or cancer that produces a soluble antigen, preferably a multi-epitopic antigen.

The present invention also includes a method for designing new therapeutic agents comprising selecting a soluble antigen, preferably an antigen that has been determined to be multi-epitopic; and selecting a binding agent that specifically binds to said antigen to form a complex. In accordance with the invention, the binding agent, the binding agent/antigen complex, and/or the antigen lead to the production of a humoral and/or cellular response in vivo. In a preferred embodiment of the invention, the method for designing a new therapeutic agent results in a binding agent or the binding agent/antigen complex that induces the production of a humoral response, as evidenced in part by the production of anti-tumor or anti-inflammation antibodies, Ab3 and/or Ab3'; and induces the production of a cellular response, as evidenced in part by the production of T-cells that are specific for the binding agent, the binding agent/antigen complex, and/or the antigen.

Although several investigators have shown that antigen-specific antibodies can enhance the immune response to those antigens presented in a complex form, the present invention is the first to demonstrate that the injection of an antibody against a single epitope can induce a multi-epic immune response in cancer patients, provided that the patients' sera contained the respective antigen. The present invention also demonstrates that this antibody injection can change the patient's immune response in such a way that the self-protein CA125 can now be recognized by the immune system.

Stimulation of T cells reactive with subdominant or cryptic epitopes of self-proteins has been suggested as an important factor in inducing immunity to a pre-determined antigen, e.g., an antigen involved in a disease or condition such as cancer or auto-immunity. Antibody-enhanced or altered presentation of an antigen, such as CA125, in an antibody complex, e.g., bound to MAb-B43.13, by B cells (antibody-specific) or macrophages c receptor mediated) may result in presentation of different peptides to the immune system than those obtained by presentation of the antigen alone. This can lead to sufficient presence of antigen-specific peptides from subdominant or cryptic epitopes which may in turn stimulate low-affinity T cells that escaped clonal deletion in the thymus or re-stimulate T cells which were suppressed. The immune response induced by exogenous administration of an antibody to a circulating self-antigen can therefore be compared to that observed in auto-immune diseases. This may also explain why presence of immune complexes of antigen with autologous human antibodies is often not correlated with improved survival. Human B cells recognize preferably immune-dominant epitopes of the antigen, leading to presentation of epitopes against which T cells were formed during fetal development. Murine antibodies on the other hand, recognize immune-dominant epitopes in mice which are not necessarily equivalent to the human immune-dominant epitopes.

The capture and processing of an antigen, e.g., PSA, by B-cells may also occur through the interaction of the membrane bound Ab2 with the anti-antigen/antigen (e.g., anti-PSA/PSA) complexes and in a similar manner through the interaction of membrane bound Ab3 with the antigen (complexed or not with the anti-PSA antibody).

Although applicants do not wish to be bound by any particular theory of operability, it is believed that the observed immunological response achieved by the present invention is attributable to an interaction between a newly formed antigen and the human patient's immune system. A portion of the immune response includes inducing the production of anti-(anti-idiotype) antibodies by the patient. Within this set of anti-(anti-idiotype) antibodies are those that are directly complimentary to the paratope of an anti-idiotype antibody. It is further believed that the paratope of the anti-idiotype antibody presents an "internal" image of the tumor cell epitope identified (i.e., selectively bound) by the idiotype antibody and, therefore, the anti-(anti-idiotype) antibodies will also bind the tumor antigen. In effect, the present method induces a immunological response to the first antigen, e.g., a tumor antigen, by presenting a second antigen (the paratope of the anti-idiotype antibody, which is essentially indistinguishable from the tumor antigen) to a portion of the patient's resulting antibodies.

Many human diseases are characterized by excessive or inappropriate immune responses. As used herein, these are undesirable or non-therapeutic effects. For example, in transplantation, the immune system attacks MHC-disparate donor tissue leading to graft rejection, in autoimmune disease it attacks normal tissues, and in allergy the immune system is hyper-responsive to otherwise harmless environmental antigens. It is now recognized that immunosuppressive therapy may be appropriate for treating each of these disorders.

The present invention concerns altering immunogenicity in a manner that produces a beneficial or therapeutically desirable effect. As used herein, a beneficial or desirable immune response is one that produces a therapeutically desirable result. For example, for a cancer such as ovarian cancer, a beneficial or desirable immune response includes the production of an antibody that immunoreacts with a previously non-immunoreactive ovarian cancer antigen. In this example, the immune response to an antigen is increased. In another example, for a condition such as inflammation, a beneficial or desirable immune response includes the production of an antibody that immunoreacts with a previously immunoreactive antigen so that it becomes non-immunoreactive. In this example, the immune response is decreased.

open bars, 0.1 µg or kU per mL; hatched bars, 1 µg or kU per mL; closed bars, 10 µg or kU per mL.

Figure 6:
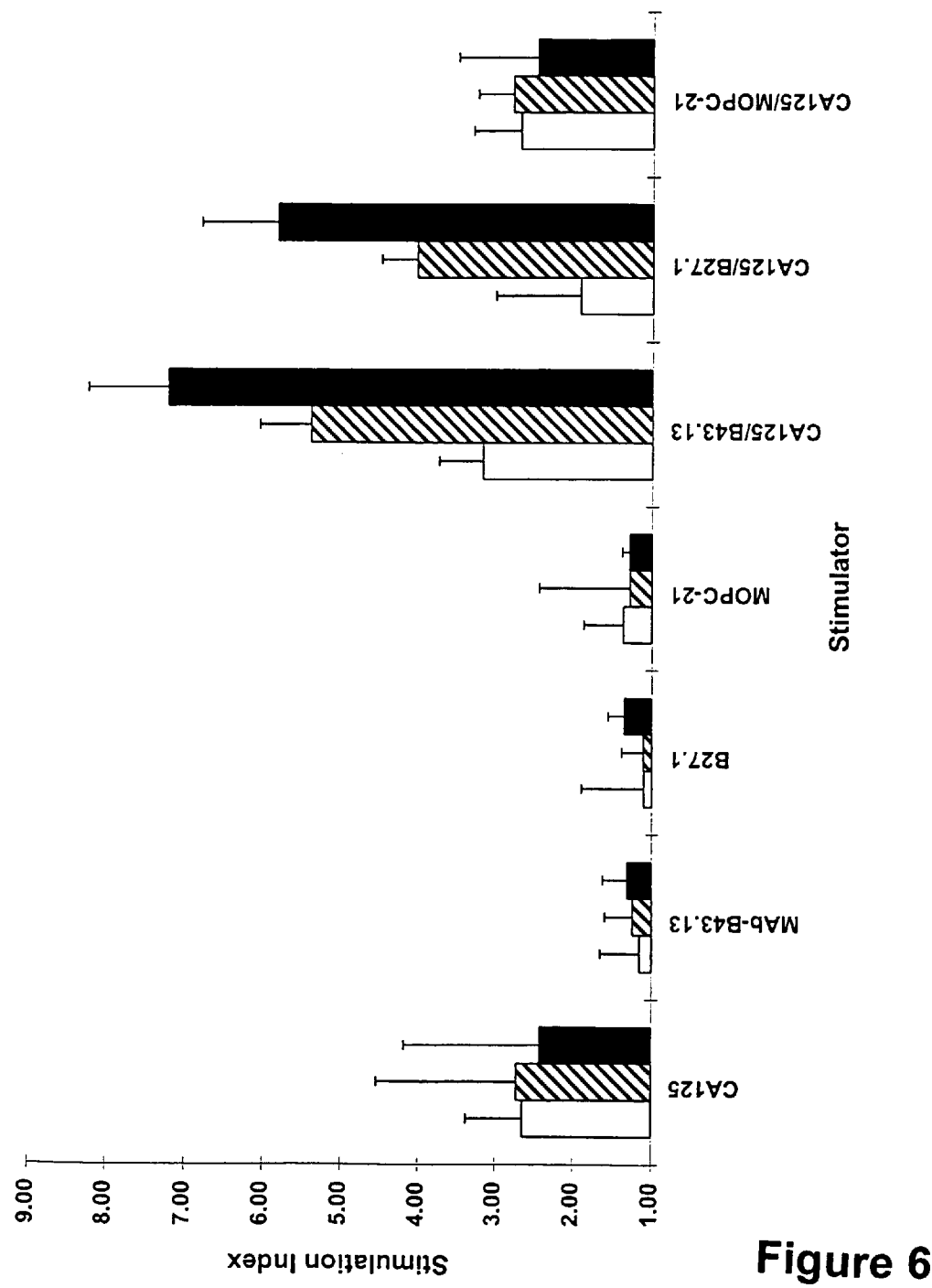

FIG. 6 shows that a binding agent/antigen complex stimulates an immune response. Legend: open bars, 0.1 µg or kU per mL; hatched bars, 1 µg or kU per mL; closed bars, 10 µg or kU per mL.

Figure 7:
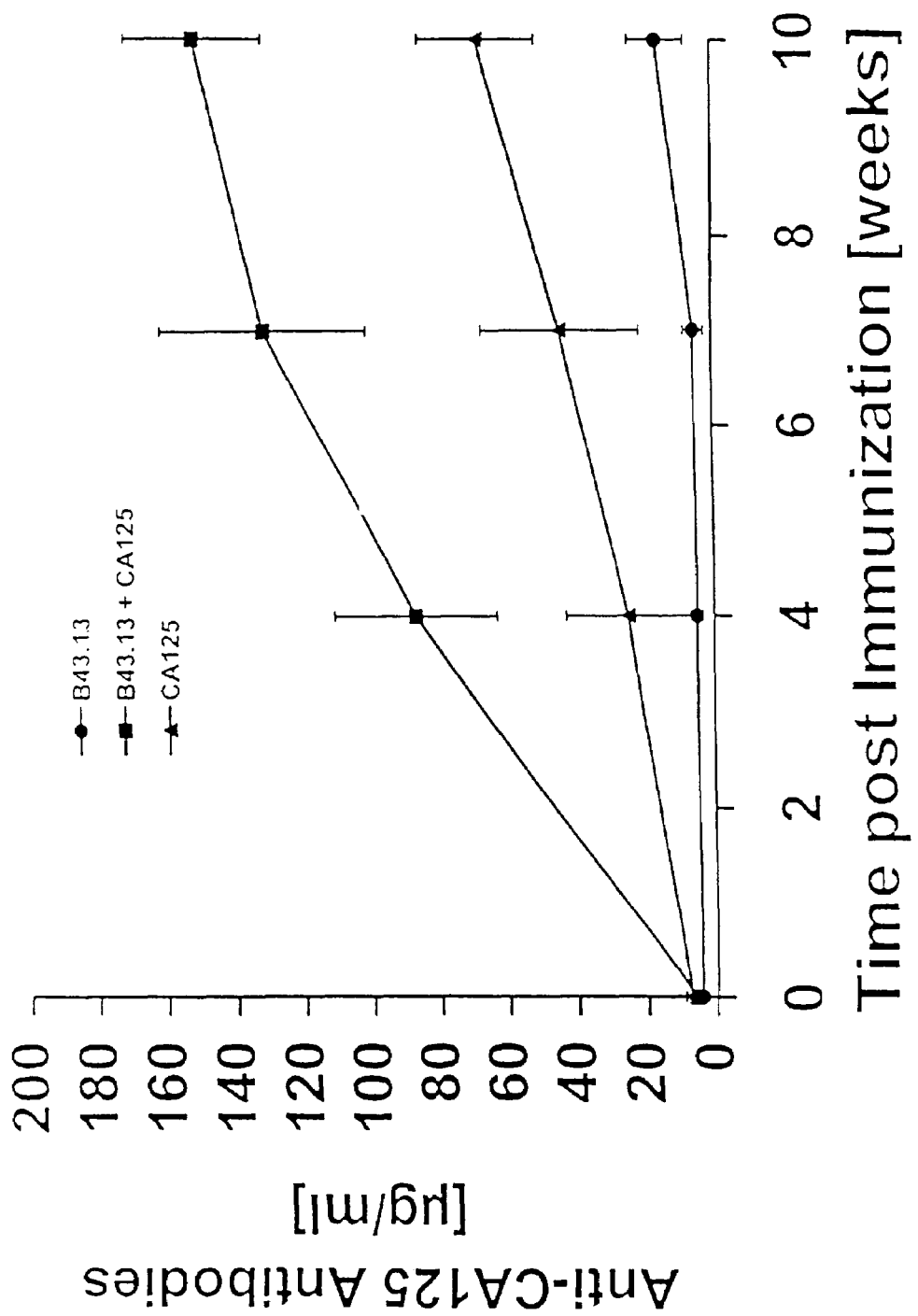

FIG. 7 shows the ability of a composition of the invention to increase the immunogenicity of its target antigen. Legend: ●, MAb 43.13; ■, MAb 43.13+CA 125; ▲, CA 125.

Figure 8:
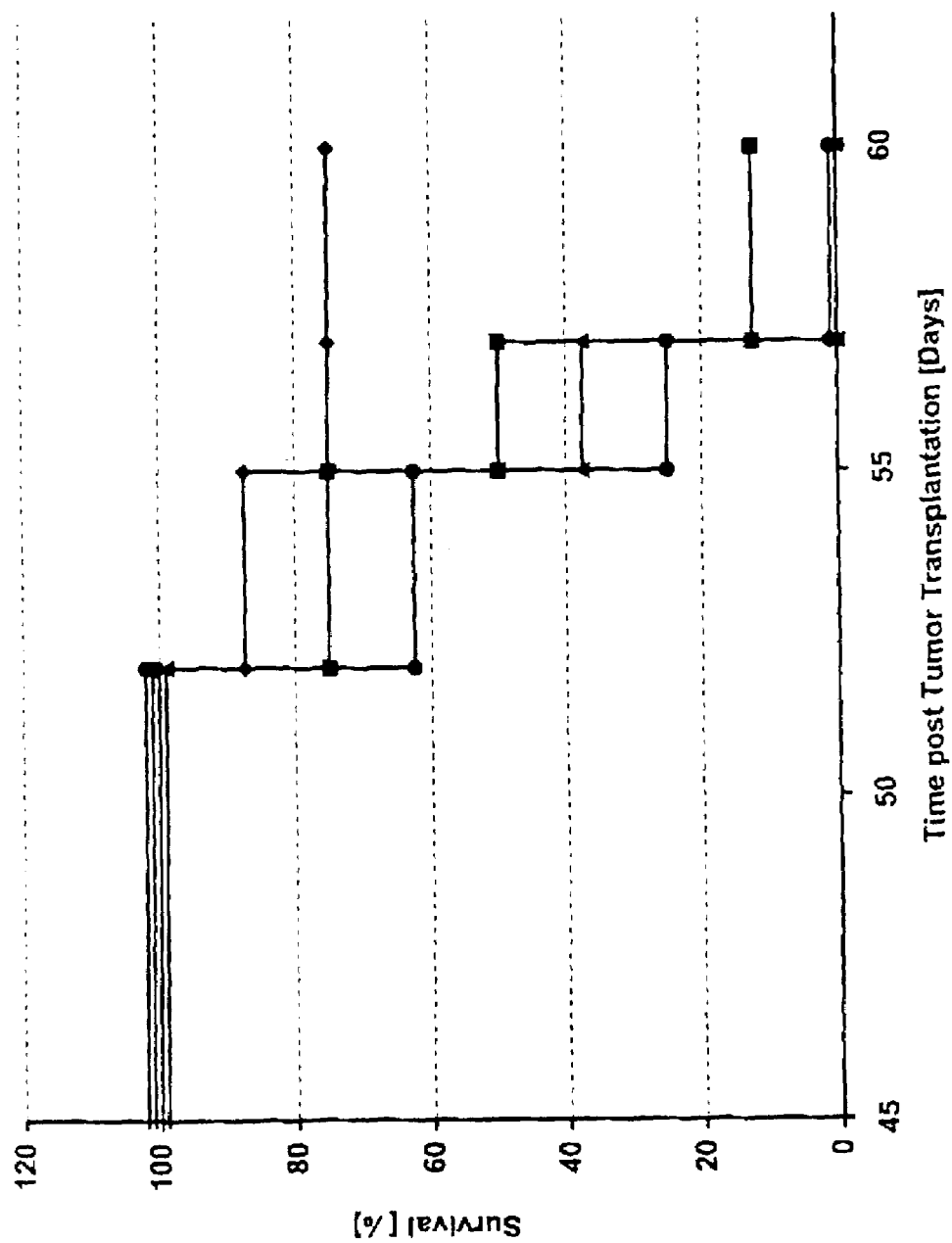

FIG. 8 shows the effect of a composition of the invention on the survival of tumor-bearing human-PBL-SCID/BG mice. Legend: ♦, MAb-B43.13+PBL; ■, MAb-170+PBL; ▲, PBS+PBL; ●, tumor only.

Figure 9:
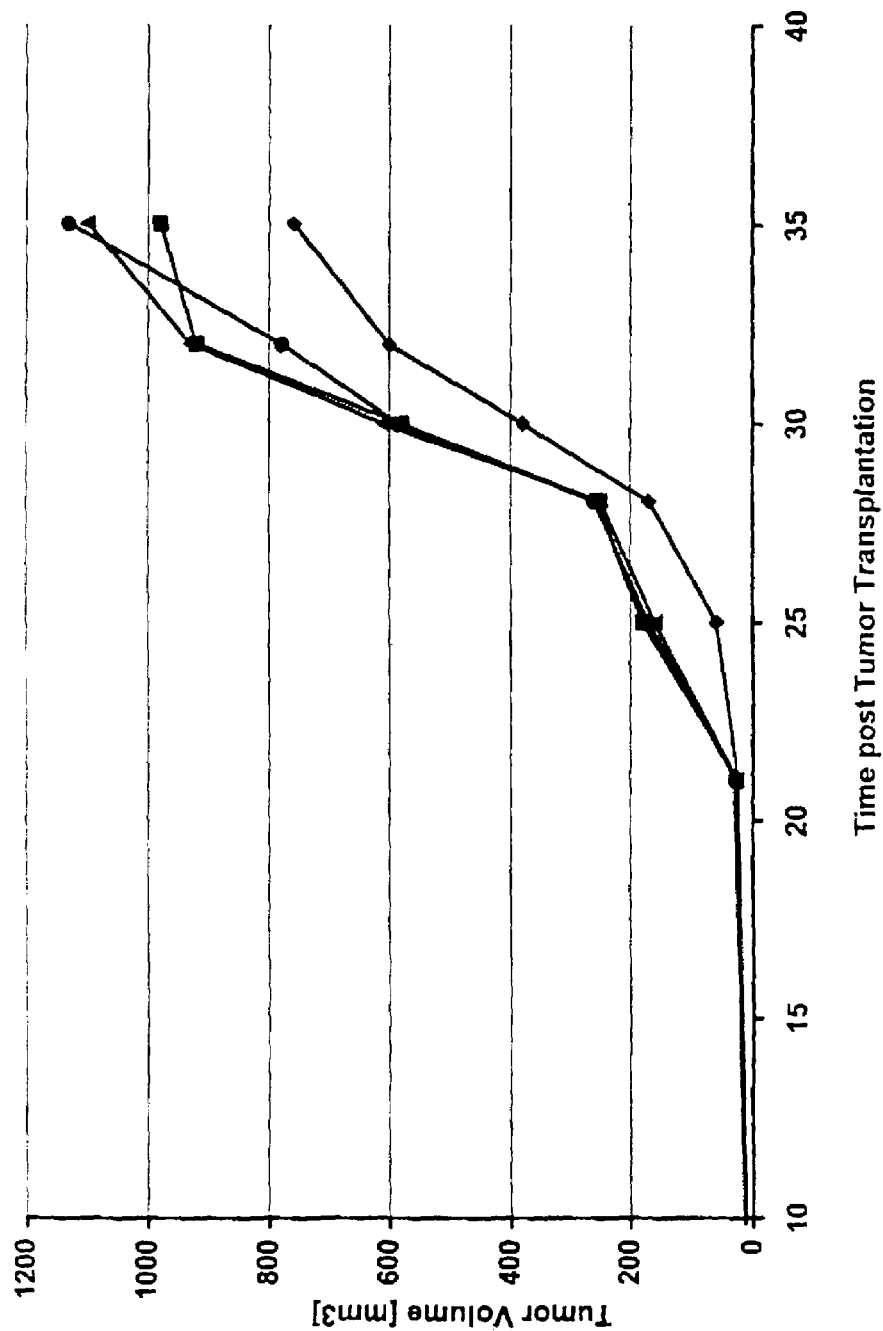

FIG. 9 shows the effect of a composition of the invention on tumor size of tumor-bearing human-PBL-SCID/BG mice. Legend: ♦, MAb-B43.13+PBL; ■, MOPC21+PBL; ▲, MAb 43.13; ●, MOPC21.

Figure 10:
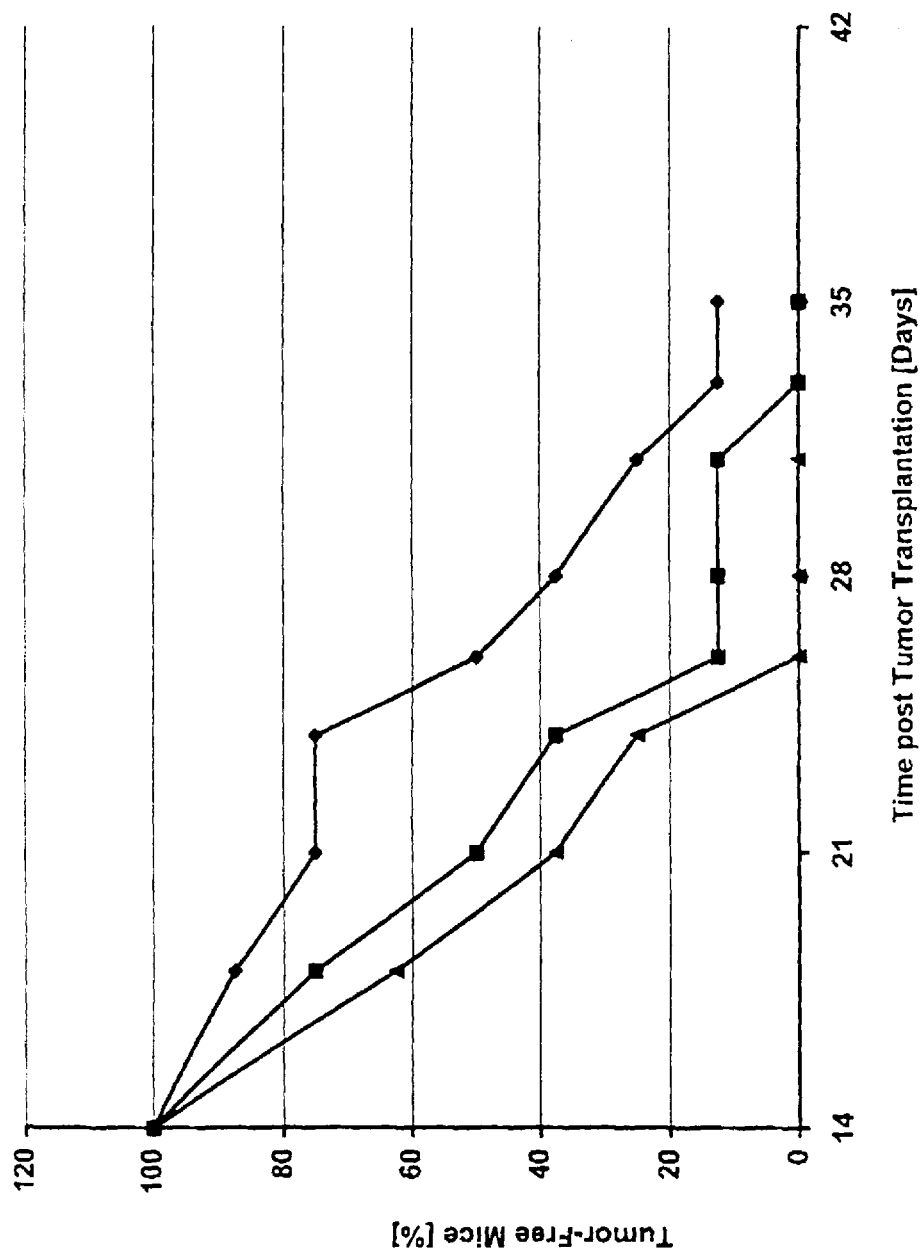

FIG. 10 shows the effect of a composition of the invention on tumor prevention for tumor-bearing human-PBL-SCD/BG mice. Legend: ♦, MAb-B43.13+PBL; ■, MOPC21+PBL; ●, tumor only.

Figure 11:
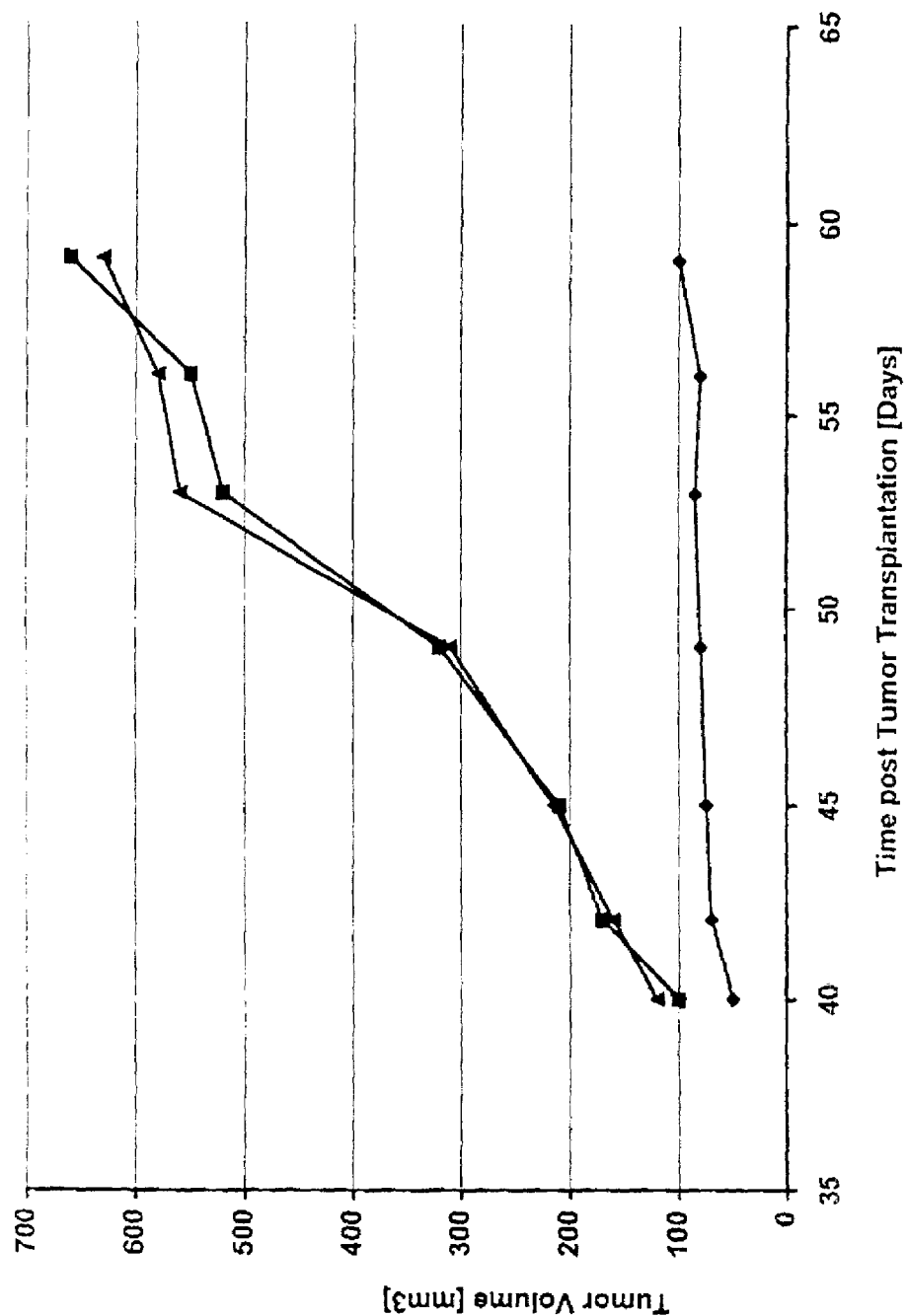

FIG. 11 shows the effect of a composition of the invention on tumor size for tumor-bearing human-PBL-SCID/BG mice. Legend: ♦, MAb-B43.13+PBL; ■, MOPC21+PBL; ●, tumor only.

Figure 12:
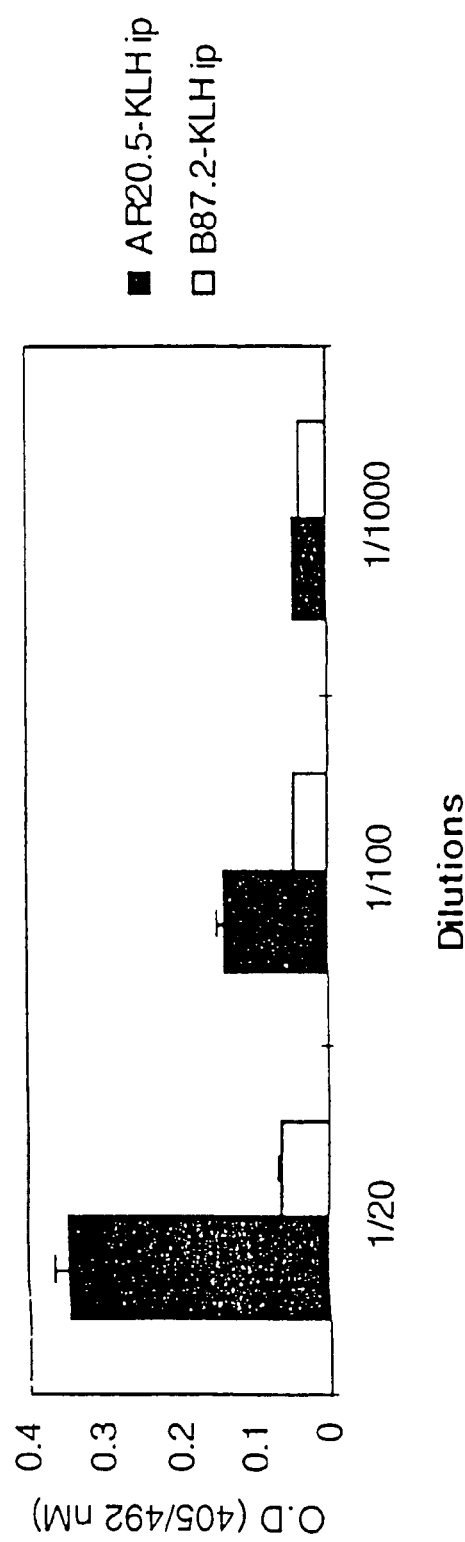

FIG. 12 shows a humoral response generated by a composition of the invention directed against breast cancer.

Figure 13:
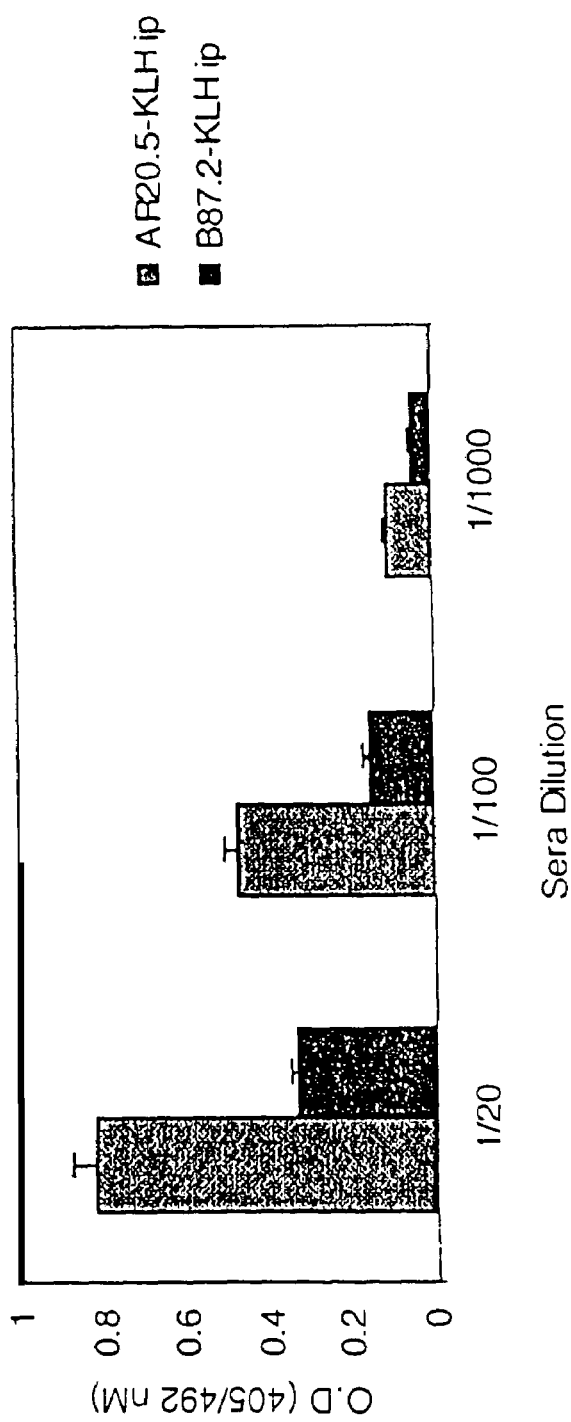

FIG. 13 shows a humoral response generated by a composition of the invention directed against breast cancer.

Figure 14:
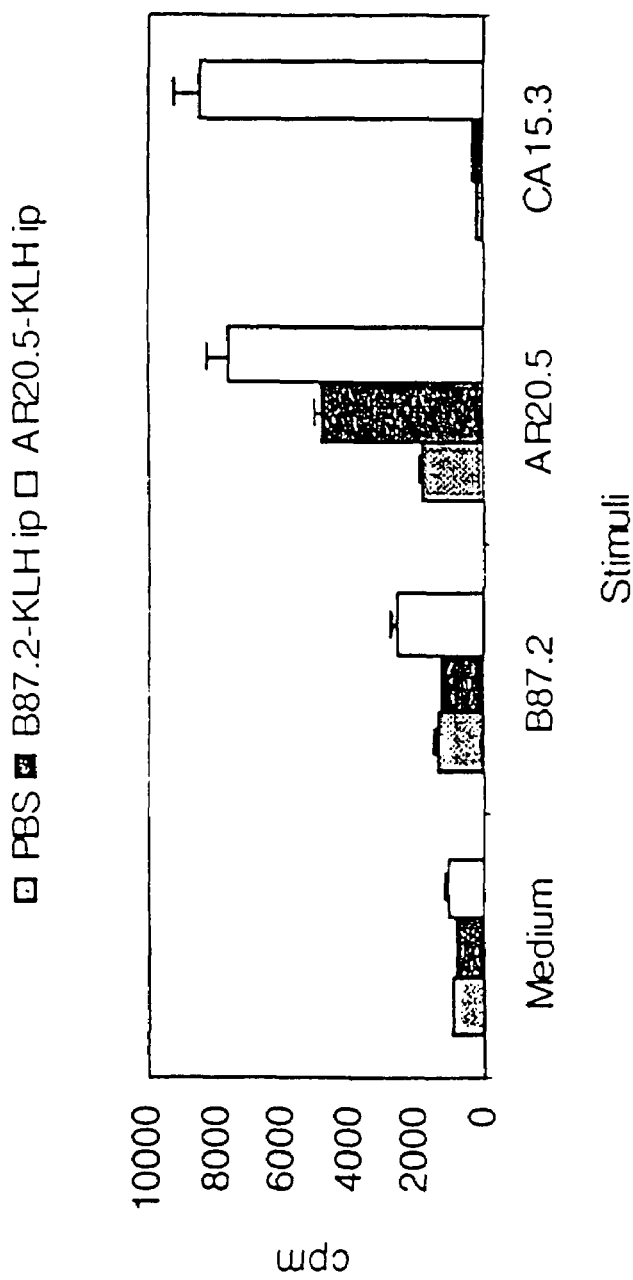

FIG. 14 shows a cellular response generated by a composition of the invention directed against breast cancer.

Figure 15:
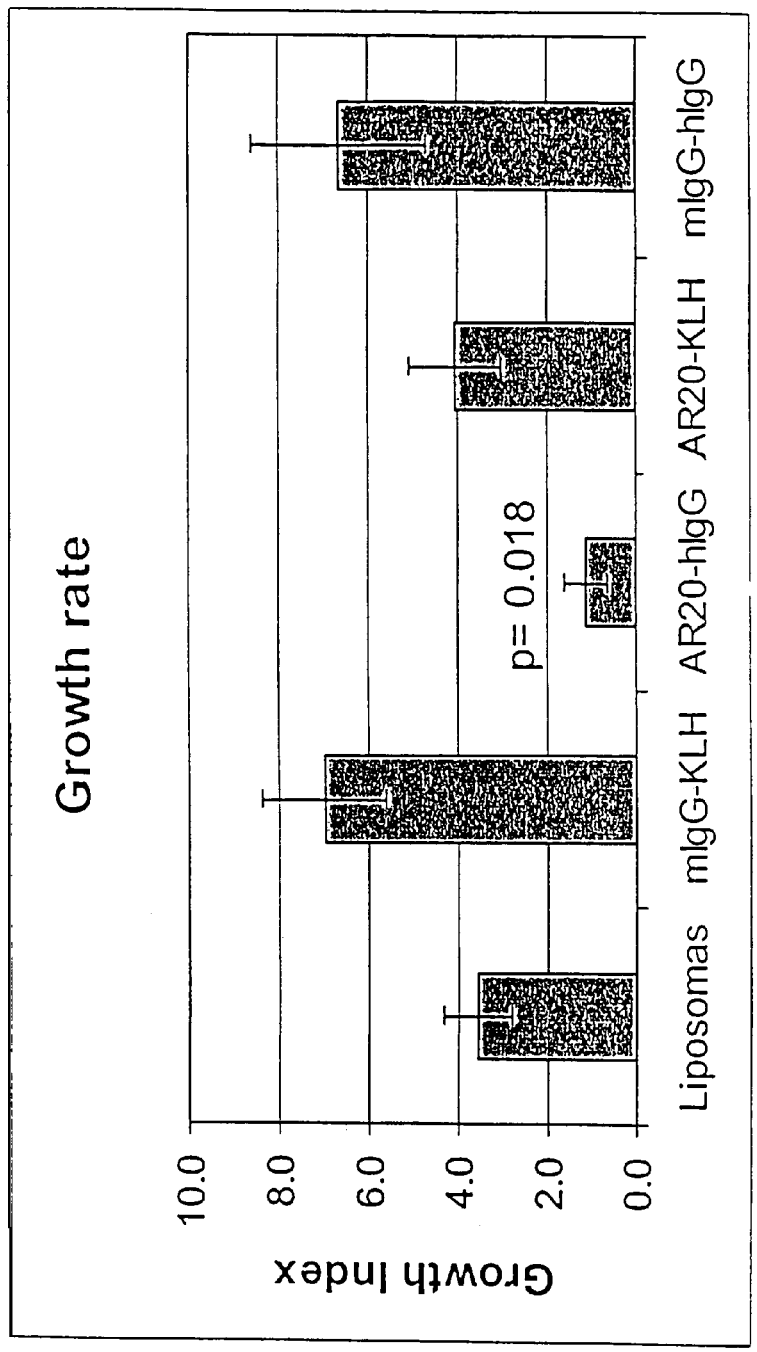

FIG. 15 shows a reduction in breast tumor growth rate after administration of a composition according to the invention.

Figure 16:
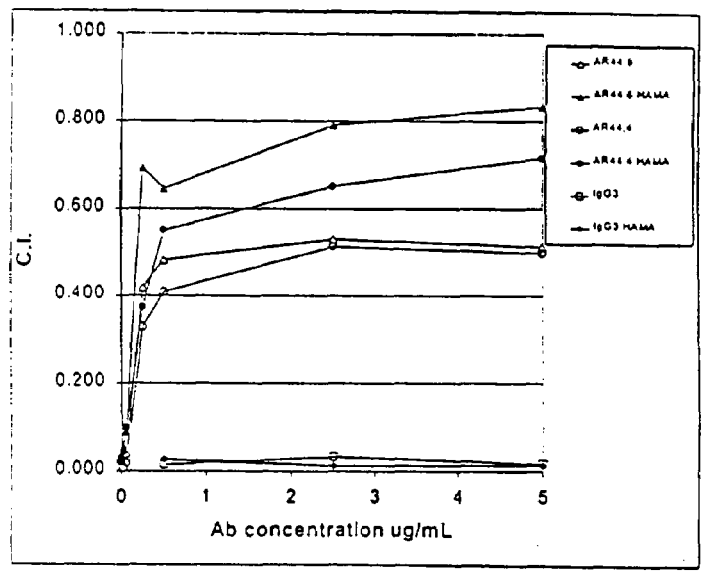

FIG. 16 shows that AR 44.6 and AR 44.4 binding agents are effective in complement-mediated cytotoxicity.

Figure 17:
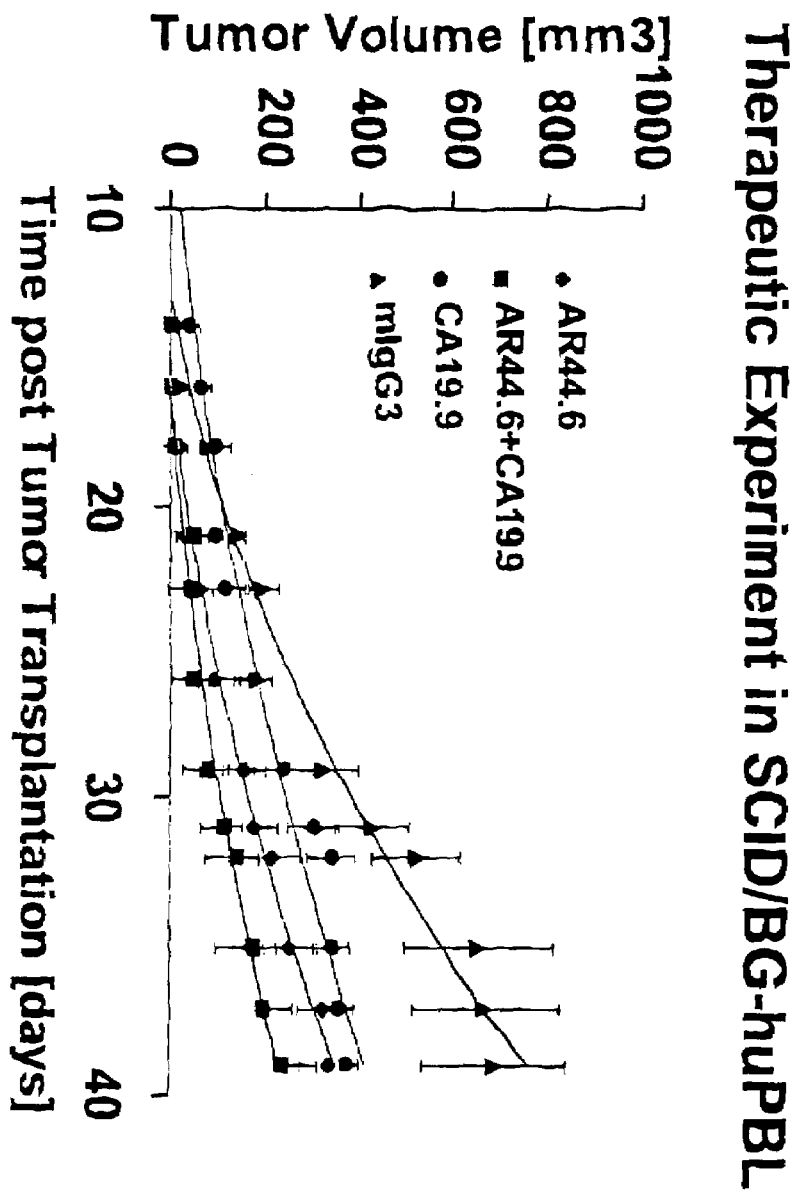

FIG. 17 shows the reduction in gastrointestinal tumor volume after administration of a composition of the invention.

Figures 18, 20:
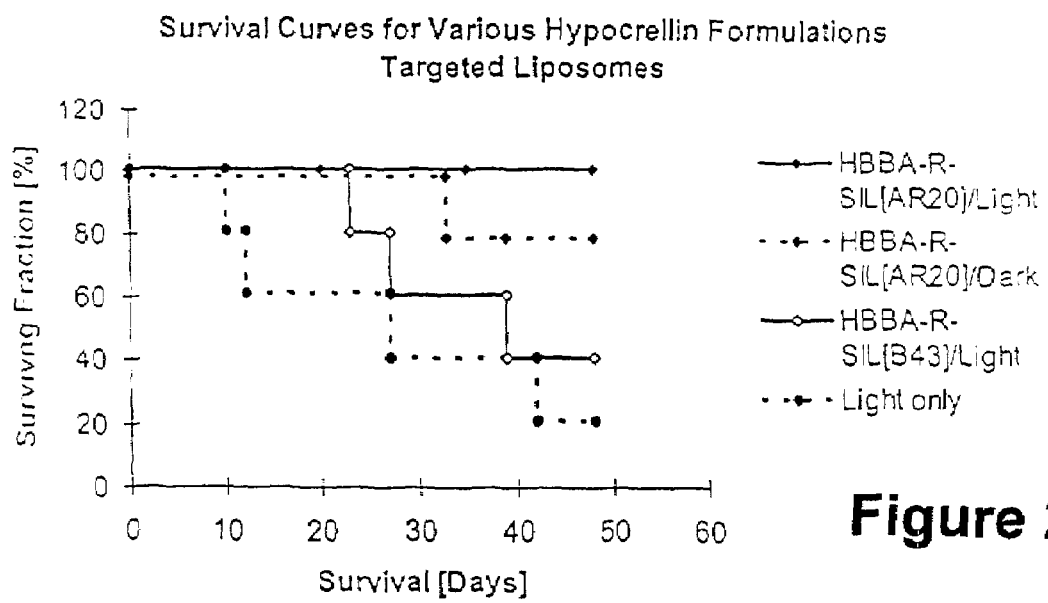

FIG. 18 shows the amino acid sequence of a prostate-specific antigen binding site.

Figure 19:
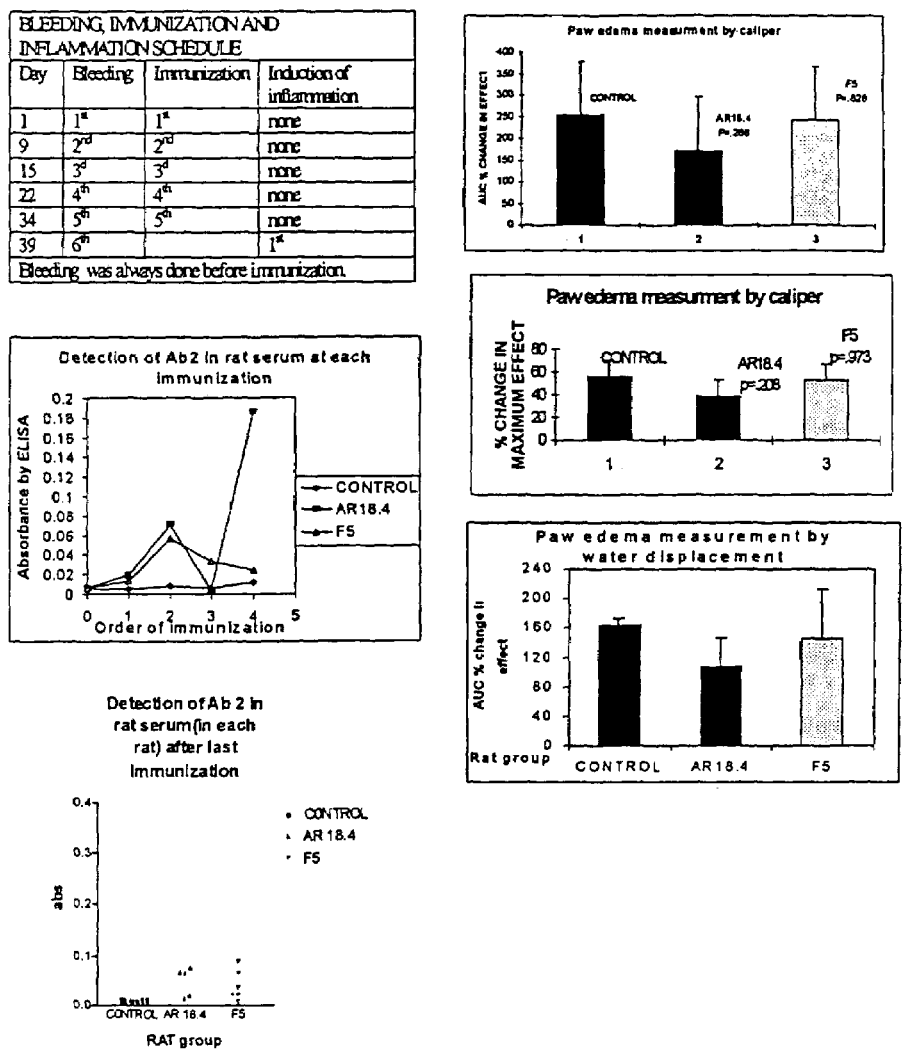

FIG. 19 shows the results and characteristics of an anti-inflammatory composition according to the invention.

FIG. 20 shows the survival curves after administering HBBA-R2-SIL, in combination with photodynamic therapy.

DISCLOSURE OF THE INVENTION

The present invention comprises a method for increasing the immunogenicity of an administered composition by target selection, by activation methodologies, and by delivery systems that, in combination, induces either cellular or humoral immunity, or both. The present invention involves the discovery that binding a binding agent to a soluble antigen, such as a multi-epitopic tumor-associated antigen, increases the immunogenicity of the immunogen while maintaining its antigenicity, and leads to the generation of a humoral and/or cellular response to the immunogen. The methods and compositions of the present invention typically allow or promote a host's ability to generate an immune response to a previously non-immunogenic antigen. In this manner, the host immune system can recognize and initiate an immune response to the previously unrecognized antigen.

An additional composition of the present invention may also include a modified antigen, wherein a soluble, preferably multi-epitopic, antigen is modified by binding to a binding agent. An additional method of the present invention may include producing the modified antigen, and/or using the modified antigen to achieve a therapeutic effect, e.g., producing or inducing an immune response against the antigen.

In accordance with the present invention, the inventors believe the interaction between the antigen and the binding agent effectively presents a previously unexposed or suppressed epitope to the patient's immune system to generate: 1) a humoral response resulting in human anti-tumor antibodies that may or may not be inhabitable by the injected antibody, but are definitely inhabitable by an antibody that binds to an epitope different from the epitope reactive with the injected BA; and 2) a cell-mediated response resulting in the production of antigen-specific T-cells.

As noted above, the inventors believe that an important aspect of generating a cellular and humoral response lies in part in increasing the immunogenicity of the binding agent-antigen complex while maintaining its antigenicity. As described in more detail below and in the Examples, increasing immunogenicity while maintaining antigenicity may be affected by one or more of the following:

1. Administering a dose of binding agent that is low in comparison to the dose for other therapeutic compositions;
2. Forming a binding agent-antigen complex in vivo or ex vivo;
3. Photoactivating the binding agent prior to administration
4. Administering the binding agent in a microsphere, liposome, nanosphere, or micelle;
5. Conjugating the binding agent to a photodynamic agent, such as hypocrellin B; and
6. Conjugating the binding agent to immune effectors.

In a preferred embodiment of the invention, a composition comprising a pre-determined antibody that specifically binds to a pre-determined tumor associated antigen is used to bind a soluble antigen produced by the tumor. Once the soluble antigen is bound, the immune system recognizes the antigen as "foreign," and mounts an immune response against the antigen or against the binding agent bound to the antigen. Antigens that can be made immunogenic are potentially useful to induce or activate an immune response, leading to therapeutic and possibly prophylactic benefits.

Any composition that includes a binding agent according to the invention may be used to initiate an in vivo immune response. The composition may include one or more adjuvants, one or more carriers, one or more excipients, one or more stabilizers, one or more imaging reagents, one or more effectors; one or more photodynamic agents; and/or physiologically acceptable saline. Generally, adjuvants are substances mixed with an immunogen in order to elicit a more marked immune response. Control vaccinations without the adjuvant resulted in humoral immune responses.

In a preferred embodiment of the invention, a suitable composition includes a binding agent that binds to a soluble antigen to form a complex that is itself antigenic and immunogenic. In a most preferred embodiment of the invention, the complex is an antigen that induces a beneficial or desirable therapeutic effect.

The composition may also include pharmaceutically acceptable carriers. Pharmaceutically accepted carriers include but are not limited to saline, sterile water, phosphate buffered saline, and the like. Other buffering agents, dispersing agents, and inert non-toxic substances suitable for delivery to a patient may be included in the compositions of the present invention. The compositions may be solutions suitable for administration, and are typically sterile and free of undesirable particulate matter. The compositions may be sterilized by conventional sterilization techniques.

In accordance with the teachings of the present invention, the methods and compositions produce both a humoral and cellular response. Those skilled in the art will readily recognize that determining that a humoral and/or cellular response has been generated is easily shown by testing for the structures associated with each response. For example, evidence of the production of a humoral response includes but is not limited to the production of Ab2 and Ab3. Likewise, evidence of the production of a cellular response includes but is not limited to the production of T2 and/or T3 cells.

Binding Agents

The binding agents of the present invention bind the soluble antigen of interest, and the resulting immunogenic pair may be used to prime or initiate an immune response to another epitope on the complex or a portion of the complex. The previously unrecognizable epitope, upon being recognized by agents of the immune system, initiates the immune system cascade that results in an immune response to the whole antigen.

A binding agent (BA), as used herein, refers to one member of an immunologic pair, e.g., a binding moiety that is capable of binding to a single epitope expressed on the tumor antigen. Exemplary binding agents include, but are not limited to: monoclonal antibodies ("MAb"); chimeric monoclonal antibodies ("C-MAb"); humanized antibodies; genetically engineered monoclonal antibodies ("G-MAb"); fragments of monoclonal antibodies (including but not limited to "F(Ab)$_2$", "F(Ab)" and "Dab"); single chains representing the reactive portion of monoclonal antibodies ("SC-MAb"); tumor-binding peptides; a protein, including receptor proteins; peptide; polypeptide; glycoprotein; lipoprotein, or the like, e.g., growth factors; lymphokines and cytokines; enzymes, immune modulators; hormones, for example, somatostatin; any of the above joined to a molecule that mediates an effector function; and mimics or fragments of any of the above. The antibody may be a polyclonal antibody or a monoclonal antibody. The binding agent may be labeled or unlabeled, but is preferably unlabeled. Antibodies and antibody fragments are preferred. In a most preferred embodiment of the invention, the binding agent is an Ab1 antibody that induces the production of one or molecules that comprise an immune response, including but not limited to one or more of the following: molecules associated with a cellular response, molecules associated with a humoral response, Ab3, Ab3', ADCC, CDC, cytokines, chemokines, cytotoxic T lymphocytes (CTL), and natural killer cells (NK).

The antibody may be obtained by immunizing any animal capable of mounting a usable immune response to the antigen, such as a mouse, rat, goat sheep, rabbit or other suitable experimental animal. In the case of a monoclonal antibody, antibody producing cells of the immunized animal may be fused with "immortal" or "immortalized" human or animal cells to obtain a hybridoma which produces the antibody. If desired, the genes encoding one or more of the immunoglobulin chains may be cloned so that the antibody may be produced in different host cells, and if desired, the genes may be mutated so as to alter the sequence and hence the immunological characteristics of the antibody produced. Fragments of binding agents, may be obtained by conventional techniques, such as by proteolytic digestion of the binding agent using pepsin, papain, or the like; or by recombinant DNA techniques in which DNA encoding the desired fragment is cloned and expressed in a variety of hosts. Irradiating any of the foregoing entities, e.g., by ultraviolet light will enhance the immune response to a multi-epitopic antigen under similar conditions. In a preferred embodiment of the invention, effector functions that mediate CDC or ADCC are not required.

One of the most promising approaches to tumor immunotherapy is to use antibody fragments or antibody fragments with effector domains to target and kill tumor cells. Single-chain Fv (scFv) has been genetically engineered as a recombinant fusion protein that is composed of a heavy chain (Vh) and a light-chain (Vl) variable domain connected by an artificial linker.

The prospect of scFv mediated bi-functional molecule is encouraging for number of reasons. If it is possible to produce them in bacteria and/or yeast expression systems then this might lead to lower costs. In general, smaller immunoglobulin forms such as scFv appear to be of greater advantage. This small molecule has shown increased accessibility to tumor cells in vivo and may therefore be better than MAb for use in drug, radionuclide or hormone delivery systems.

The Fv fragments of immunoglobulins have many significant advantages over whole immunoglobulins for the purpose of medical imaging and for targeted tumor therapy, including better lesion penetration on solid tumor tissue and more rapid blood clearance, as well as potentially lower Fc-mediated immunogenicity. The single-chain Fv (scFv) in this study was engineered from the genes isolated from the variable regions of anti-CA125 (tumor marker expressed in 80% of all ovarian carcinomas) antibody.

In an embodiment of the invention, a suitable composition for the treatment of an ovarian tumor associated antigen contains a binding agent that binds the CA 125 antigen. Exemplary binding agents that bind to CA 125 include antibody B43.13 produced by the mouse hybridoma B43.13 (MCB-ALT-96), which was deposited with the American Type Culture Collection (ATCC), 10801 University Blvd., Manassas, Va. 20110-2209, on May 18, 2000, and was given ATCC deposit number PTA-1883. In another embodiment of the invention, a suitable composition for the treatment of gastrointestinal cancer contains a binding agent that binds the CA 19.9 antigen. In yet another embodiment of the invention, a suitable composition for the treatment of breast cancer contains a binding agent that binds the CA 15.3 antigen. Various binding agents, antibodies, antigens, and methods for preparing, isolating, and using the antibodies are described in U.S. Pat. No. 4,471,057 (Koprowski) and U.S. Pat. No. 5,075,218 (Jette, et al.), both incorporated herein by reference. Furthermore, many of these antibodies are commercially available from Centocor, Abbott Laboratories, Commissariat a L'Energie Atomique, Hoffman-LaRoche, Inc., Sorin Biomedica, and FujiRebio.

As noted in the background section, the potential effect of injecting a binding agent such as an antibody can be extremely complex and may typically involves distinct mechanisms of action. As used in herein, Ab3 and Ab3' represent two such distinct mechanisms that individually and/or collectively produce a beneficial effect. In the Ab3 pathway, an Ab1 antibody that is capable of binding to a pre-determined antigen may induce the production of an anti-idiotype antibody (Ab2β) that mimics an epitope of the antigen. The anti-idiotype antibody in turn may induce the production of anti-anti-idiotype antibodies (Ab3) that are capable of binding the same epitope on the antigen as the Ab1 antibody. Evidence of this pathway includes a competitive assay between Ab1 and Ab3, since the Ab1 antibody and the antibody compete for the same epitope of the antigen.

In the Ab3' pathway, the Ab1 antibody binds to the antigen to form a complex. This complex is itself an antigen, and is sometimes described herein as a "modified antigen" or second antigen. The complex may induce the production of anti-antigen antibody (Ab3') that are capable of binding a different epitope on the antigens as that bound by the Ab1 antibody. Evidence of this pathway also includes a competitive assay, but comparing the inhibitory effect on Ab3' by antibodies that bind to different epitopes on the antigen or lack of inhibition with Ab1.

In addition to producing Ab3 and/or Ab3', typically associated with a humoral immune response, the compositions of the present invention may also produce a therapeutic benefit by inducing a cellular immune response (cell mediated immunity), as in the Background section. Both the cellular and the humoral response involve indirect mechanisms for altering the immunogenicity of the host.

Compositions of the present invention may also initiate direct mechanisms for killing undesirable cells such as cancer cells. For example, in antibody-dependent cell-mediated cytotoxicity (ADCC), an Ab1 antibody, bound through its Fab region to a pre-determined antigen, may bind to the Fc receptor of a lymphocyte through the Fc region of the Ab1 antibody. Such participation between an antibody and immune system cells produces an effector function that may lyse tumor cells, infectious agents, and allogeneic cells. Other indirect mechanisms involve complement-mediated cytotoxic (CDC), apoptosis, neutralization of immunosuppressive tumor-associated antigens, induction of cytokines and/or chemokines, neutralization of immunosuppressive molecules, and neutralization of anti-adhesion molecules, among others.

As used herein, a comprehensive approach to providing a therapeutic benefit involves one or more, or all, of the following: cellular immunity and the molecules involved in its production; humoral immunity and the molecules involved in its production; ADCC immunity and the molecules involved in its production; CDC immunity and the molecules involved in its production; natural killer cells; cytotoxic T lymphocytes, and the molecules and cells involved in their production; and cytokines and chemokines, and the molecules and cells involved in their production.

Soluble Antigen

The binding agent may be directed against any antigen of clinical significance, but preferably is directed against a tumor-associated antigen (TAA). In the case of TAA, the cancer may include, but is not limited to lung, colon, rectum, breast, ovary, prostate gland, head, neck, bone, immune system, or any other anatomical location. The subject may be a human or animal subject. Illustrative tumors and tumor markers are listed in U.S. Pat. No. 5,075,218.

The methods of the present invention involve any cancer that produces a soluble multi-epitopic TAA. As used herein soluble is used to describe any antigen that is detectable in a body fluid, i.e., blood, serum, ascites, saliva, or the like. In accordance with the present invention, the preferred tumors are those that: shed soluble tumor antigens, e.g., tumor antigens shed into the bloodstream, as opposed to a surface antigen or an intracellular antigen; exhibit a multi-epitopic tumor associated antigen, preferably of carbohydrate or glycoprotein (e.g., mucin) nature; and can be found at a concentration in the patient's body fluid more than is normally present in healthy controls and such a high level signifies a poor prognosis for the patient, yet has not initiated an immune response. As is well known by one skilled in the art, one method of determining whether the concentration of the TAA is greater than is predictive of recurrence of the disease is by comparing the patient's concentration to that of a healthy control. If the concentration of the TAA is higher than the healthy control, then the patient's concentration is predictive of poor prognosis of the disease.

The invention also involves the production of a modified antigen, typically by producing the modified antigen in vivo. As used herein, modified antigen refers to a first antigen, typically invisible to the immune system, that binds to a binding agent, and the binding agent-antigen is itself an antigen (the "second" antigen) that is immunoreactive with one or more molecules of the immune system.

A used herein, "disease" refers to the management, diagnosis, and/or palliation of any mammalian (including human) disease, disorder, malady, or condition. "Disease" includes but is not limited to cancer and its metastases, such as skin cancer; growths or tumors, and their metastases; tumors and tumor cells, such as sarcomas and carcinomas, including solid tumors, blood-borne tumors, and tumors found in nasal passages, the bladder, the esophagus, or lung, including the bronchi; viruses, including retroviruses and HIV; bacterial diseases; fungal diseases; and dermatological conditions or disorders, such as lesions of the vulva, keloid, vitiligo, psoriasis, benign tumors, endometriosis, Barett's esophagus, *Tinea capitis*, lichen amyloidosis drugs of abuse, multiple sclerosis, allergy, autoimmune diseases, and asthma. Exemplary soluble multi-epitopic antigens are described above, and include but are not limited to CA 125, CA 19.9, CA 15.3, and prostate specific antigen.

Immunogenicity Enhancers

1. Low Dose

In accordance with the methods of the present invention, a composition comprising the binding agent may be administered in an amount sufficient to recognize and bind the pre-determined antigen, such as a tumor associated antigen (TAA), preferably a soluble multi-epitopic antigen. In a preferred embodiment of the invention, the dosage is sufficient to generate or elicit an immune response against the antigen. See Example 20. An immunologically or therapeutically effective or acceptable amount of binding agent is an amount sufficient to bind a pre-determined antigen in vivo or ex vivo, and is capable of eliciting an immune response to the antigen. The response inhibits or kills tumor cells that carry and present a newly accessible epitope, thereby ameliorating or eliminating the disease or condition that produces the antigen. The immune response may take the form of a humoral response, a cell-mediated response, or both. In a preferred embodiment of the invention, the dosage of the monoclonal antibody is less than the dosage required to elicit ADCC or CDC.

The concentration or dosage of the protein in the composition can vary widely, e.g., from less than about 0.01% to about 15 to 20% by weight. As noted above, the composition is administered in an amount sufficient to stimulate an immune response against the antigen. Amounts effective for this use will depend in part on the severity of the disease and the status of the patient's immune system. Generally, the composition will include about 0.1 µg to about 2 mg or more of protein agent per kilogram of body weight, more commonly dosages of about 1 µg to about 200 µg per kilogram of body weight, recognized by those skilled in the art as comprising a low dose. Further, those skilled in the art will recognize and be able to evaluate the various considerations that may be used to determine a proper dose. The concentration will usually be at least 0.5%; any amount may be selected primarily based on fluid volume, viscosity, antigenicity, etc., in accordance with the particular mode of administration.

2. Photoactivation

In accordance with the present invention, an antibody may be photoactivated. Processes for photoactivating a binding agent are extremely well known in the art, and include exposing the antibody to radiation, wherein the resulting altered antibody is capable of generating an immune response when administered to an animal typically capable of generating an immune response to the native form of the antibody.

In a preferred embodiment of the invention, the antibody is exposed to ultraviolet light. Typically, the antibody may be exposed to ultraviolet light at a wavelength from about 200 nm to about 400 nm, at from about 0.1 to about 1000 Joules/cm$^2$, for from about 1 to about 180 minutes (more preferably, about 10 to about 30 minutes).

3. Delivery System

Since some binding agents such as proteins are by themselves poor immunogens, their immunogenicity may be augmented by administration in immunological adjuvants and antigen delivery systems. The immunogenicity of a specific composition may also be increased or optimized by choice of delivery route. For example, the immunogenicity of compositions produced in accordance with the present invention that include a monoclonal antibody may be increased by choosing a mode of delivery that increases the direct contact between the binding agent and the antigen. The preferred route is intravenous. Those skilled in the art are conversant with the various choices available, and why one route might be chosen over another route for a particular binding agent.

One skilled in the art will also recognize that liposomes, nanospheres, micelles, or microspheres may be used to administer a composition, and that such administration may increase immunogenicity.

4. Photosensitizer

Compositions of the present invention may include one or more photosensitizers. Exemplary photosensitizers include, but are not limited to fluorescein, hematoporphyrin derivatives (e.g., Photofrin®), porphyrin derivatives, and perylenequinoid pigments. In a preferred embodiment of the invention, the photosensitizer comprises the use of perylenequinone (PQP) derivatives as photodynamic agents, and the use of PQP derivatives in immunophotodynamic therapy (IPT).

The invention also comprises a method of treating a disease by administering a therapeutically sufficient amount of at least one PQP derivative bound to a binding agent, and activating the conjugate, typically by photoactivating the PQP derivative. Typically, the PQP derivative may be activated by exposing the derivative to a pre-determined wavelength of light. The invention also includes a method of treating cancer which is enhanced in the presence of light wavelengths between about 400 nm and about 850 nm. Suitable PQPs include, but are not limited to those disclosed in U.S. Ser. No. 08/782,048, incorporated herein by reference. In a preferred embodiment of the invention, the PQP is hypocrellin B, molecules derived from HB, and compositions that include HB or one or more of its derivatives.

The desired characteristics for a PDT sensitizer comprise at least one or more of the following characteristics: good absorption of light in a wavelength that penetrates tissue to the desired depth (absorption in the 600 nm to 850 nm range penetrate the skin many mm), compound sensitive to pH—inactive, lower activity or activity destroyed at the pH characteristic of normal tissues, but active or higher activity at the pH of the cells or organisms to be treated; compound cleared from the body quickly and if a compound is intended to treat solid tumors it should have the ability to function either in the presence and/or absence of oxygen to address the problem of tumor cell hypoxia. The photosensitizer should have low dark cytotoxicity, and excellent photopotentiation of cellular damage. The PDT toxic effect may be mediated via necrotic, apoptotic cell death, or by stasis of the tumor vasculature or vascular bed.

5. Effectors

The present invention includes a composition comprising a binding agent bound to or used in conjunction with one or more effectors. As used herein, effector refers to a substance that affects the activity of the binding agent without binding to the substrate (or antigen) binding site.

A conceptually straightforward method to functionalize recombinant antibodies consists of sequentially fusing the antibody gene with the gene of a second protein, and expressing the resulting fusion protein as a single protein. Exemplary second proteins include but are not limited to:

a. A signal amplification moiety, such as a biotin mimetic sequence, which can be introduced at the C-terminus of a binding agent as a detection tag because of strong affinity of streptavidin-biotin;

b. liposomes: fuse certain amino acid sequences (with negative charges under physiologic condition) with a binding agent, such as single chain Fv-B43.13. Therefore, the fusion protein can easily be trapped by liposomes;

c. cytokine sequences (e.g. IL-2): IL2 is a lymphokine synthesized and secreted primarily by T helper lymphocytes which have been activated by stimulation of the T cell receptor complex with antigen/MHC complexes on the surfaces of antigen-presenting cells. The response of T helper cells to activation is induction of the expression of IL2 and of receptor of IL2. IL2 possesses a variety of other activities which affect B cell growth and differentiation, formation of LAK cells, and augmentation of NK cells and enhancement of their cytolytic activity. Because of the central role of the IL2/IL2 receptor system in mediation of the immune response, it is obvious that manipulation of this system has important therapeutic implications. IL2 has already shown promise as an anti-cancer drug by its ability to stimulate the proliferation and activities of tumor attacking LAK and TIL cells.

d. toxin: immunotoxins made by attaching a toxin (e.g. Pseudomonas extoxin and bacteria RNase) to the antibody or antibody fragments to produce cytotoxic molecules that selectively kill target tumor cell.

e. enzyme: an antibody-directed enzyme pro-drug therapy system is a particularly attractive artificial effector method. In this approach, an antibody is used to target an enzyme to the tumor, and to retain it while the antibody-enzyme conjugate clears from normal tissues. A non-toxic pro-drug is then administrated, and this is activated by the enzyme to produce a cytotoxic drug at the tumor site.

f. radionuclide chelator: any peptide that binds to a radionuclide chelator, e.g., metallothionein (MT). MT is a ubiquitous, low-molecular weight, metal-binding protein that participates in metal metabolism and detoxification. Mammalian forms of MT bind seven ions in tetrahedral metal-thiolate clusters, including technetium and other metals useful for targeted radiodiagnosis or therapy. The highly conserved MT structure offers the additional advantage of low-to-nonexistent immunogenicity.

G. A phagocytosis enhancer, e.g., tuftsin. Tuftsin is natural tetrapeptide (Thr-Lys-Pro-Arg) that was found to manifest several biological activities, including activation of macrophages/monocytes and stimulation of phagocytosis. It has a wide spectrum of immunoadjuvant activities which it exerts on the phagocytic cells, the polymorphonuclear leukocyte, the monocyte and the macrophage. In animal and clinical studies, tuftsin has displayed anti-tumor, anti-infection activity with no detectable toxicity.

The fusion protein scFv-tuftsin was defined as a recombinant fusion protein that is composed scFv antibody binding domain connected with tuftsin by an artificial linker. This bi-functional protein was designed to achieve higher specific anti-idiotypic immunogenicity. The strategies used to produce scFv-tuftsin protein relied on the methylotrophic yeast *P. pastoris* expression/secretion system that has been developed to the overproduction of a variety of eukaryotic proteins with high secretion-efficiency. In this system, a foreign gene is inserted in the place of the *P. pastoris* alcohol oxidase (AOX1) gene and the expression of the cloned gene is thus under the control of the strong and methanol inducible AOX1 gene promoter.

Method

As used herein, "administering" refers to any action that results in exposing or contacting a composition containing a binding agent with a pre-determined cell, cells, or tissue, typically mammalian. As used herein, administering may be conducted in vivo, in vitro, or ex vivo. For example, a composition may be administered by injection or through an endoscope. Administering also includes the direct application to cells of a composition according to the present invention. For example, during the course of surgery, tumor cells may be exposed. In accordance with an embodiment of the invention, these exposed cells (or tumors) may be exposed directly to a composition of the present invention, e.g., by washing or irrigating the surgical site and/or the cells.

For diseases that can be characterized in part by having a tumor-associated antigen that is multi-epitopic, the present invention involves contacting a soluble antigen with a binding reagent (BA) that specifically binds to a single epitope on the multi-epitopic tumor-associated antigen.

In accordance with a method of the invention, the binding agent must be capable of binding a pre-determined binding site or receptor, and may be administered to the patient by any immunologically suitable route. For example, the binding agent may be introduced into the patient by an intravenous, subcutaneous, intraperitoneal, intrathecal, intravesical, intradermal, intramuscular, or intralymphatic routes. The composition may be in solution, tablet, aerosol, or multiphase formulation forms. Liposomes, long-circulating liposomes, immunoliposomes, biodegradable microspheres, micelles, or the like may also be used as a carrier, vehicle, or delivery system. Furthermore, using ex vivo procedures well known in the art, blood or serum from the patient may be removed from the patient; optionally, it may be desirable to purify the antigen in the patient's blood; the blood or serum may then be mixed with a composition that includes a binding agent according to the invention; and the treated blood or serum is returned to the patient. The clinician may compare the anti-idiotypic and anti-isotypic responses associated with these different routes in determining the most effective route of administration. The invention should not be limited to any particular method of introducing the binding agent into the patient.

Administration may be once, more than once, and over a prolonged period. As the compositions of this invention may be used for patient's in a serious disease state, i.e., life-threatening or potentially life-threatening, excesses of the binding agent may be administered if desirable. Actual methods and protocols for administering pharmaceutical compositions, including dilution techniques for injections of the present compositions, are well known or will be apparent to one skilled in the art. Some of these methods and protocols are described in *Remington's Pharmaceutical Science*, Mack Publishing Co. (1982).

A binding agent may be administered in combination with other binding agents, or may be administered in combination with other treatment protocols or agents, e.g., chemotherapeutic agents.

The effectiveness of the proteins of the present invention may be monitored in vitro or in vivo. Humoral responses may be monitored in vitro by conventional immunoassays, where the anti-tumor activity of the response may be determined by complement-mediated cellular cytotoxicity and/or antibody-dependent cellular cytotoxicity (ADCC) assays. The assay methodologies are well know, and are described in *Handbook of Experimental Immunology*, Vol. 2, Blackwell Scientific Publications, Oxford (1986). Other assays may be directed to determining the level of the antigen in the patient or tissue. Cell-mediated immunity may be monitored in vivo by the development of delayed-type hypersensitivity reactions, or other in vivo or in vitro means known to those skilled in the art, including but not limited to the skin test reaction protocol, lymphocyte stimulation assays, measuring the toxicity of a subject's lymphocytes to tumor cells by using a standard cytotoxicity assay, by a limiting dilution assay, or by measuring plasma levels of cytokines using standard ELISA assays.

Determining the effectiveness of a specific binding agent—antigen pair may also be accomplished by monitoring cell killing. Those skilled in the art will recognize that there are a variety of mechanisms that are proof of cell killing. As shown in the Examples, cell killing may be demonstrated by showing that Ab3 mediates ADCC, that Ab1 and HAMA mediates CDC, that natural killer (NK) cells are produced, and/or that cytotoxic T lymphocytes (CTLs) are produced.

The mouse hybridoma AR20.5R8233, which produces monoclonal antibody AR 20.5, was deposited with ATTC, 10801 University Blvd., Manassas, Va. 20110-2209, on 23 Nov. 1999. The mouse hybridoma B43.13: MCB-ALT1-96, which produces monoclonal antibody B43.13, was deposited with ATTC, 10801 University Blvd., Manassas, Va. 20110-2209, on 18 May 2000.

EXAMPLES

Example 1

Antibody Mediated Immunotherapy Influence of Circulating Antigen in Inducing Antigen Specific Anti-Tumor Immune Responses This example demonstrates the use of antigen-specific murine monoclonal antibodies to induce an immune response against an immune-suppressive tumor-associated antigen. Injecting an antibody against a specific epitope in a multi-epitopic antigen can lead to immune responses against various other epitopes on this antigen.

In an attempt to understand the mechanism of action of MAb-B43.13, various immunological parameters were studied in patients injected with this antibody. These studies clearly demonstrated activation of both the humoral and cellular anti-cancer immune responses.

Figure 1:
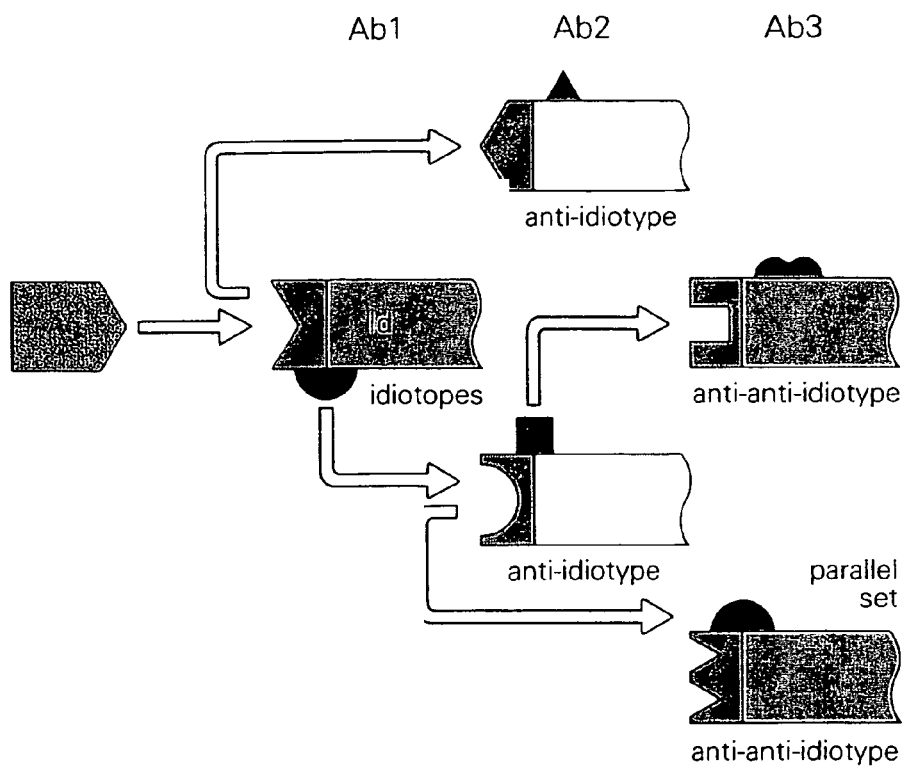
FIG. 1 is a graphic representation of the different types of antibodies and their structural relationship to each other and to an antigen.
Figure 2:
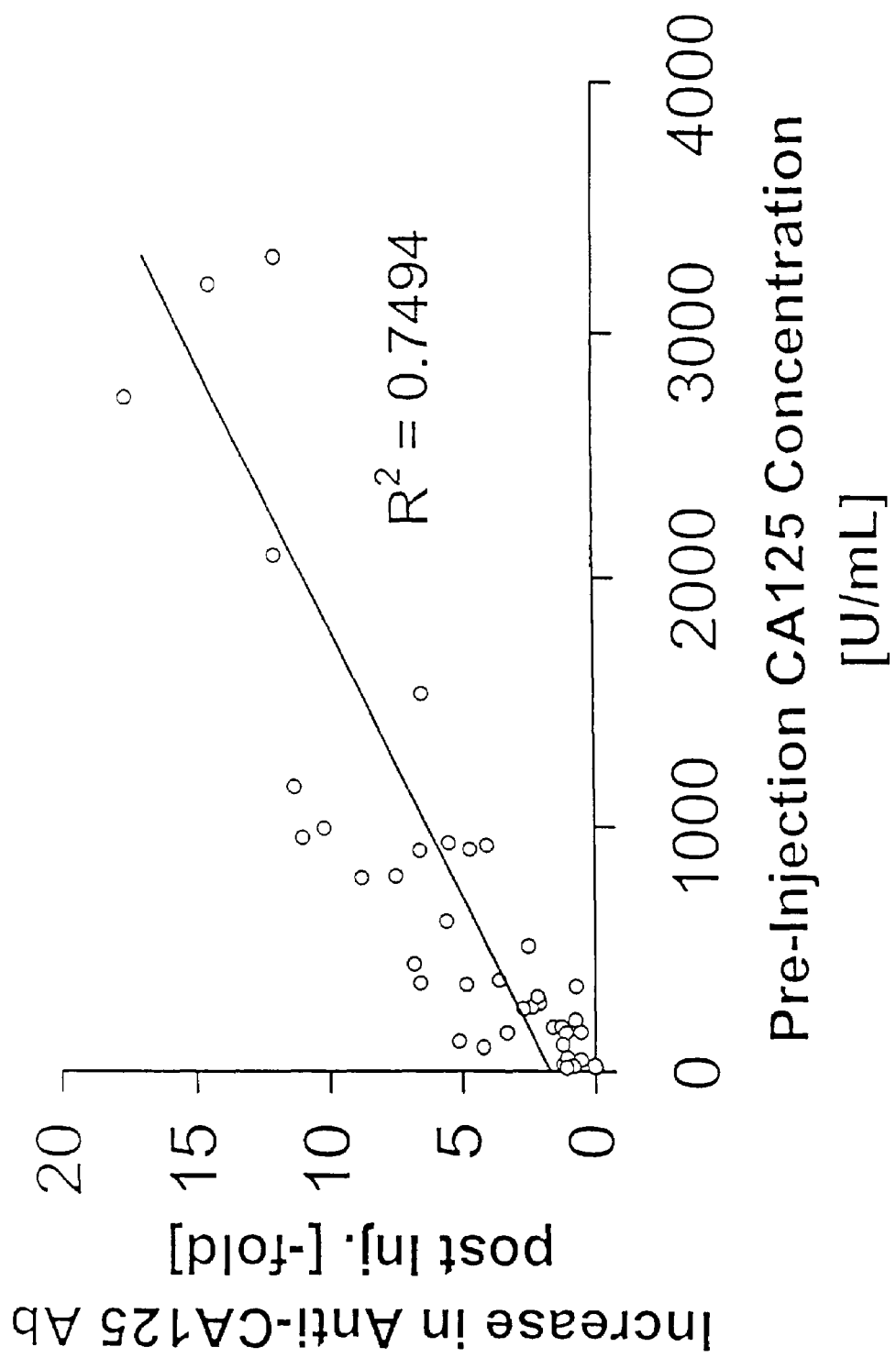
FIG. 2 shows that a composition of the invention induces an immune response against a tumor associated antigen.

The generation of human CA125-binding antibodies was measured before and after MAb-B43.13 injection and correlated to pre-injection CA125 levels as well as to survival data. Tables 1 and FIG. 2 show that generation of anti- CA125 antibodies correlates with CA125 pre-injection levels. Circulating CA125 affects the development of anti-CA125 antibodies only when patients received the MAb-B43.13 injection. If anti-CA125 antibodies before injection of MAb-B43.13 are compared between patients with low or high CA125 values (below or above 100 U/mL), no difference was found between the two groups (Table 1). A minimum concentration of 100 U/mL of CA125 was found to be necessary to see a statistically significant difference in the anti-CA125 response.

Figure 3:
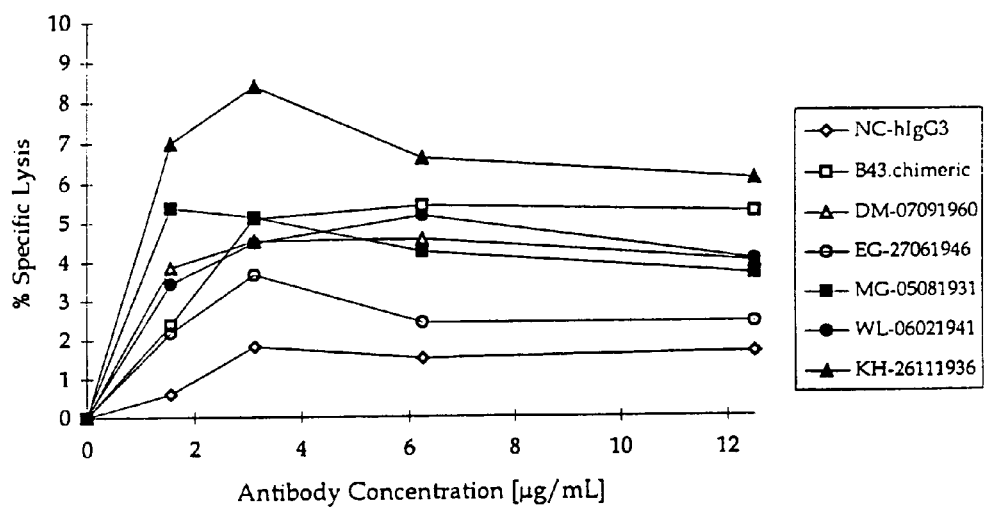
FIG. 3 shows tumor cell lysis caused by administering a composition of the present invention.

Further, an increase in anti-CA125 antibodies was correlated with improved survival prognosis (Table 2). The difference in survival between anti-CA125 responders and non-responders was found to be statistically significant. The observation that MAb-B43.13 treated patients with high CA125 values had a better survival prognosis than those with low CA125 titers is very interesting, especially in view of reports indicating that high levels of mucin-like antigen is correlated with poor prognosis. Among patients with no humoral response to CA125, high circulating antigen levels were correlated with lower survival rates, as expected from the literature. In the other hand, high circulating CA125 levels were not considered a bad prognostic factor in patients, who developed anti-CA125 antibodies after MAB43-13 injection (Table 2). Anti-CA125 antibodies purified from these patients not only bound to human ovarian cancer cells but also mediated tumor killing via antibody-dependent cell-mediated cytotoxicity (ADCC). See FIG. 3. It should be emphasized in this context that only one patient out of 52 showed detectable anti-CA125 antibodies before injection.

TABLE 1

| Anti-CA125 Titer [ng/mL] Mean ± SD | Anti-CA125 Titer [ng/mL] Median | No. of Positives/ Total | % Positives | Significance P |
|---|---|---|---|---|
| No MAbB43.13 Injection | | | | |
| CA125< 100 U/mL | 54.8 ± 27.5 | 45 | 0/14 | 0 | |
| CA125> 100 U/mL | 94.8 ± 212.7 | 50 | 1/38 | 2.63 | 0.264 |
| After MAb-B43.13 Injection | | | | |
| CA125< 100 U/mL | 100.0 ± 56.7 | 72.5 | 1/21 | 4.76 | |
| CA125> 100 U/mL | 242.3 ± 327.1 | 137.5 | 15/50 | 30.0 | 0.0072 |

TABLE 2

| | Survival [months] | | Significance |
|---|---|---|---|
| | Mean ± SD | Median | P |
| Anti-CA125 non-responders | 37 ± 18 | 38 | |
| CA125< 100 U/mL | 44 ± 26 | 40.5 | |
| CA125> 100 U/mL | 30 ± 14 | 30 | 0.3283 |
| Anti-CA125 responders | 70 ± 43 | 49 | |
| CA125< 100 U/mL | 57 ± 22 | 45.5 | |
| CA125> 100 U/mL | 83 ± 48 | 58 | 0.0088 |
| Anti-CA125 non-responders CA125< 100 U/mL | 44 ± 26 | 40.5 | |
| Anti-CA125 responders CA125> 100 U/mL | 57 ± 22 | 45.5 | 0.2014 |

TABLE 2-continued

| | Survival [months] | | Significance |
|---|---|---|---|
| | Mean ± SD | Median | P |
| Anti-CA125 non-responders | 30 ± 14 | 30 | |
| Anti-CA125 responders | 83 ± 48 | 58 | 0.0009 |

In an attempt to understand the mechanism behind anti-CA125 antibody formation by MAb-B43.13 injection in cancer patients, we characterized the human anti-CA125 antibodies present in their sera. For example, if the anti-CA125 antibodies were generated in the manner suggested by the idiotypic network, MAb-B43.13 would generate anti-MAb-B43.13 antibodies, some of which would exactly mimic the CA125 antigen (=Ab2β). These in turn can generate anti-CA125 antibodies (=Ab3). The Ab3 generated through this pathway would bind to the same epitope on CA125 as the Ab1 (=B43.13) and therefore compete with the binding of MAb-B43.13 to the antigen.

On the other hand, antibodies generated through the antigen itself will bind to various epitopes available on the antigen. If the anti-CA125 antibodies were generated in a manner suggested by the present invention, the pathway would follow Ab1+soluble antigen→Ab3'. Following this scheme, MAb-B43.13 (Ab1) would bind the CA125 serum antigen, which would in turn generate an anti-CA125 antibody (Ab3'). Furthermore, the Ab3' antibodies generated under this pathway would bind and be inhibited by other anti-Ca 125 antibodies, such as B27.1, because, as noted above, CA125 is multi-epitopic and B43.13 and B27.1 epitopes are distinct; also, Ab3' will not bind to anti-MAb-B43.13 antibodies.

Analysis of the serum samples with positive anti-CA125 titers demonstrated that their binding to CA125 could be inhibited not only by MAb-B43.13 single chain antibody but also by F(ab') fragments of other anti-CA125 antibodies, B27.1 and M11, that recognize epitopes on CA125 which are different from B43.13 (Table 3). Sera from only two patients were considered to contain anti-CA125 antibodies that were exclusively generated via idiotype induction of MAb-B43.13 (=Ab3) i.e. anti-CA125 antibodies that could only and completely be inhibited with MAb-B43.13 and bound to polyclonal rabbit Ab2.

The presence of a multi-epitopic anti-CA125 response in sera of MAb-B43.13 treated patients with high CA125 levels make us believe that, besides anti-idiotype induction, other mechanisms exist to induce an immune response against tumor-associated antigens. In this scenario, the injected antibody forms a complex with the circulating antigen in circulation. This process can cause several effects. The complexation of the antigen by antibodies can facilitate the uptake of CA125 by professional antigen-presenting cells (APC) and thus render the antigen more immunogenic. The complexing antibody—in our case from a murine source—could also function as an adjuvant, adding a foreign component to the self-antigen CA125 that might facilitate recognition by the immune system. Epitopes of the antigen are blocked by the complexing antibody and are either protected from processing or processed at different sequences thus creating new peptides for MHC-binding. It is also possible that a conformational change in the antigen takes place upon antibody binding thereby exposing new epitopes to the immune system, including sub-dominant or immune-dormant epitopes.

It is interesting to note that the complex formation between CA125 and MAb-B43.13 has also been observed during pharmacokinetic studies, as determined by drop in circulating CA125 levels upon injection of MAb-B43-13. When patients received more than one injection and patients developed high amounts of human anti-mouse antibodies (HAMA), the antibody showed rapid clearance to liver and spleen, as demonstrated in immunoscintigraphic studies. Antigen-antibody complexes, accumulated in lymphoid centers like the spleen, are known to be very efficiently presented to T cells by antigen-presenting cells like B cells or macrophages.

Augmentation of antigen processing and presentation by immune complexing has been demonstrated in several systems. Targeting tetanus toxoid to FcγR by compexing with anti-tetanus toxiod IgG results in a 10-1000-fold increase in processing and presentation of this antigen as measured by $T_H$ cell activation. A similar increase in immunogenicity was observed with hepatitis B antigen complexed with its corresponding antibody. Also the natural presence of antibodies against α-galactosyl epitopes has been used to augment tumor vaccine immunogenicity in α-galactosyl-modified tumor-associated antigens.

It was observed that MAb-B43.13 has a protective effect on its CA125 epitope during antigen processing by the immune system. The MAb-B43.13 epitope was recognized by almost all anti-CA125 antibody samples from patients (inhibition in 82% of the samples, Table 3).

Figure 4:
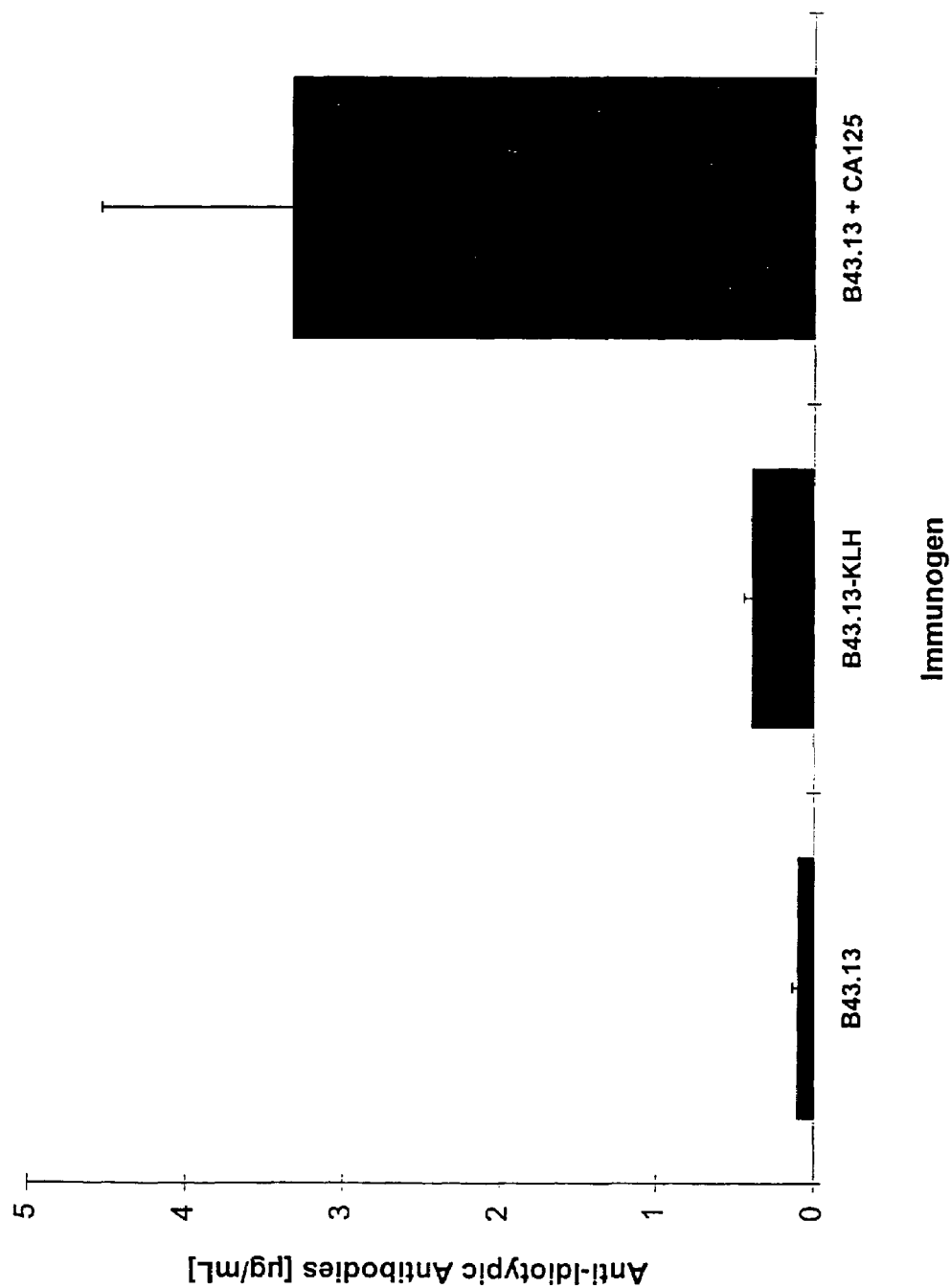
FIG. 4 shows the production of Ab2 in response to the administration of a composition of the invention.

The reverse seems to be true as well, i.e. CA125 has conserving properties on the idiotope of MAb-B43.13 during the antigen processing event. The increased formation of Ab2 in mice immunized with the CA125-MAb-B43.13 complex compared to mice immunized with MAb-B43.13-KLH (FIG. 4) and the increased Ab2 production in MAb-B43.13 injected patients with CA125 titers above 100 U/mL confirm this observation. See Table 3 for a summary and Table 4 for the details of these results. Sera from these patients were analyzed for the presence of human anti-CA125 antibodies by their ability to bind to CA125 [R. Madiyalakan et al, *Hybridoma*, 14:199-203 1995) and Schultes et al., *Cancer Immunology and Immunotherapy* 46:201-212 (1998)].

TABLE 3

| | Inhibition | | |
| --- | --- | --- | --- |
| | No. of Positives/Total | | |
| | (%) | | |
| CA125 10000 U/ml | B43.13 scFv 1 μg/ml | B27.1 F(ab') 1 μg/ml | M11 F(ab') 1 μg/mL |
| 26/28 (92.8) | 23/28 (82.1) | 19/28 (67.9) | 12/18 (66.7) |

TABLE 4

Characterization of Anti-CA125 Antibodies in Patients Injected with MAb-B43.13

| Patient | Inj.# | Days Elapsed After Injection | Anti-CA125 Ab levels | Binding to Anti-MAb-B43.13 (Ab2)† | Inhibition [%]* CA125 10000 U/mL | B43.13 s. chain** 10 μg/mL | B27.1 F(ab')** 1 μg/mL | Classification |
| --- | --- | --- | --- | --- | --- | --- | --- | --- |
| 1 | 3 | 0 | 14.8 | + | 62.3 | 42.6 | 5.8 | Ab3 |
| 2 | 1 | 185 | 9.5 | − | 21.6 | −46.9 | −86.9 | Ab3' |
| 3 | 3 | 86 | 25.4 | + | 80.2 | 84.4 | −0.5 | Ab3 |
| | 3 | 207 | 48.7 | + | 91.4 | 94.0 | −9.1 | Ab3 |
| | 4 | 144 | 79.7 | + | 77.1 | 93.0 | 3.5 | Ab3 |
| | 4 | 270 | 30.9 | + | 79.2 | 83.0 | −55.8 | Ab3 |
| | 4 | 309 | 16.7 | + | 77.0 | 83.0 | −55.8 | Ab3 |
| | 5 | 134 | 64.1 | + | 89.1 | 83.3 | −37.3 | Ab3 |
| 4 | 2 | 15 | 23.6 | − | 62.3 | −84.8 | −101.9 | Ab3' |
| | 2 | 41 | 21.6 | − | 56.9 | 20.2 | −7.0 | Ab3' |
| | 2 | 76 | 23.1 | − | 63.6 | 29.4 | 4.5 | Ab3' |
| | 3 | 28 | 11.1 | − | 24.2 | 4.7 | 11.1 | Ab3' |
| 5 | 1 | 16 | 15.5 | + | 74.8 | 78.3 | 39.9 | Ab3'/Ab3 |
| 6 | 3 | 0 | 10.3 | + | 54.0 | 60.2 | 22.7 | Ab3'/Ab3 |
| 7 | | | 14.9 | − | 29.7 | −70.2 | −358.9 | Ab3' |
| 8 | 1 | 7 | 59.1 | − | 77.1 | 87.1 | 34.9 | Ab3' |
| | 1 | 17 | 46.9 | − | 78.4 | 86.5 | 40.7 | Ab3' |
| 9 | 3 | 112 | 9.2 | − | −66.4 | 16.0 | 20.2 | Ab3' |
| | 3 | 166 | 8.5 | − | −18.4 | 42.5 | 56.5 | Ab3' |
| 10 | 3 | 0 | 41.5 | − | 30.8 | 39.2 | 20.0 | Ab3' |
| 11 | 5 | 134 | 8.8 | − | 19.0 | 24.4 | 3.5 | Ab3' |
| | 6 | 134 | 8.7 | − | 18.0 | 39.0 | 46.0 | Ab3' |
| | 9 | 26 | 13.4 | − | 54.5 | 19.3 | 11.1 | Ab3' |
| | 9 | 65 | 13.3 | − | 56.1 | 24.4 | 3.7 | Ab3' |
| | 10 | 40 | 9.4 | − | 61.4 | 37.0 | 33.4 | Ab3' |
| 12 | 2 | 14 | 10.6 | − | 24.5 | −54.4 | 19.9 | Ab3' |
| 13 | 1 | 15 | 11.5 | − | 30.8 | 47.4 | 55.8 | Ab3' |
| 14 | 2 | 17 | 10.1 | − | 30.3 | −51.2 | 1.2 | Ab3' |

*To be considered to be significant, inhibition has to be at least 10%
**Single chain MAb-B43.13 and F(ab') MAb-B27.1 were used in the inhibition studies to avoid non-specific inhibition due to the Fc portion of the antibody and cross-reactivity due to HAMA.
†Anti-MAb-B43.13 (Ab2) was purified from rabbits injected with MabB43.13.

Therefore, complex formation can lead to enhanced anti-CA125 as well as anti-idiotypic antibody formation. Manca et al., *J. Immunol.* 140:2893 (1988) and Ling et al., *Immunology* 62:7 (1987) have shown that antibodies can preserve the sequence of their epitope during antigen-processing and antibodies have been used to raise immune responses to less immunogenic epitopes of an antigen.

Figure 5:
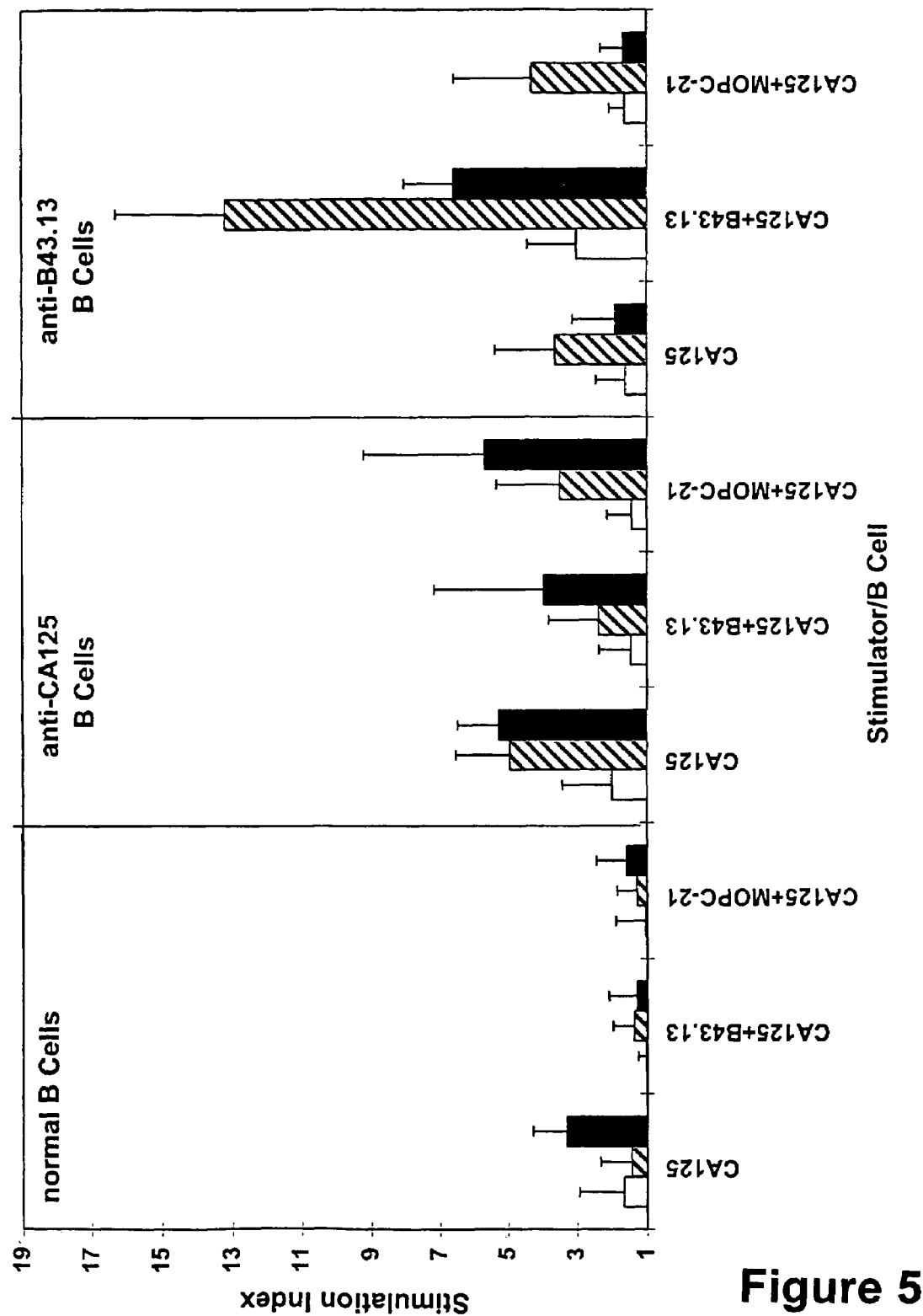
FIG. 5 shows the production of B cells in response to the administration of a composition of the invention. Legend.

Enhanced antigen-presentation of antigen-antibody complexes was attributed to facilitated antigen uptake via the Fcγ-receptor (macrophages, dendritic cells) or membrane-bound Ig (B cells) on professional antigen-presenting cells (APC). The human FcγRI and RIII-receptor on macrophages and dendritic cells does not bind murine $IgG_1$, but the human FcγRII, which mediates phagocytosis and pinocytosis of small immune complexes, has strong affinity to this murine IgG isotype. Accordingly, various professional APC can be involved in the preferential presentation of the CA125-MAb-B43.13 complex. We tested B cells with two different specificities as well as macrophages as APC: CA125-specific B cells (from mice immunized with CA125) and anti-MAb-B43.13-specific B cells (from mice immunized with MAb-B43.13). Normal B cells served as control. When the proliferation of CA125-specific T cells was monitored by [methyl-$^3$H]-Thymidine uptake, optimal stimulation was observed in MAb-B43.13 specific B cells, primed with the CA125-MAb-B43.13 complex (FIG. 5), followed by presentation of CA125 by CA 125-specific B cells. Enhanced presentation of immune complexes by macrophages and dendritic cells is mediated by preferential uptake via the FcγR. FIG. 6 confirms that CA125 is presented more efficiently by macrophages, if complexed with an antigen specific antibody.

Thus, if the patients serum contained anti-CA125 antibodies that were inhabitable by MAb-B43.13 only, it was classified as containing Ab3; those inhabitable by MAb-B27.1 were classified as Ab3'. In other words, injecting a binding agent such as an antibody against a single epitope on a multi-epitopic antigen leads to generation of a humoral and cellular response against a different epitope on the antigen.

The ability of MAb-B43.13 to increase the immunogenicity of Ca125 was studied in a mouse model by immunizing a mouse with the Ca125-MAb43.13 complex, compared to CA125 or MAb-B43.13 alone as the immunogen. When the mouse sera was analyzed for anti-CA125 antibody levels, the mice injected with the antigen-antibody complex had the highest titers (see FIG. 7). This supports the observation that interaction of the antigen with a specific antibody leads to a higher antigen specific humoral immune response compared to antibody or antigen alone.

These results clearly indicate that when an antibody against a single epitope (B43.13) was injected into a patient, an antibody response against the whole antigen is generated which recognizes different epitopes present in the antigen. The presence of Ab3 in some patients could be explained by the likely presence of excess B43.13 epitope in the CA125 due to insufficient binding of the antibody to that portion of the B 43 epitope or idiotype induction through Pathway I. Nevertheless, the predominant mechanism of the response seems to be through Pathway II. In other words, injecting a binding agent such as a monoclonal antibody to a soluble multi-epitopic antigen into a patient having a functioning immune system generates an antibody to the antigen, where the generated antibody is inhibited by antibodies to different epitopes.

Example 2

Similarly, injecting the binding agent to the cancer patients having circulating CA125 lead to antigen specific CTL's. Peripheral Blood Mononuclear Cells (PBMC) from eight patients injected with MAb-B43.13 were tested for cytotoxicity against CA125 positive or CA125 negative ovarian tumor cells in a chromium release assay. The results are shown in Table 5. The specificity of the lysis was confirmed by the ability of MAb-B43.13 to inhibit such lysis, as well as the inability to kill CA125 negative tumor cells. Of the 8 patients who received MAb-B43.13, at least four patients (#5 to #8) were determined to have CA125 specific cytotoxic T lymphocytes (CTL's) in their blood. The generation of CA125 specific CTL's are likely to kill ovarian tumor cells in patients.

TABLE 5

Cytotoxicity In Patients Injected With A Vaccine Containing MAb-B43.13

| PATIENT ID | SAMPLE Injection Number | Days Post Injection | PERCENT LYSIS CAOV-4 | SK-OV-3 | K562 | PERCENT INHIBITION BY MAb-B43.13 (5 µg) | PERCENT DIFFERENCE BETWEEN CA 125 positive and CA 125 negative CELLS |
|---|---|---|---|---|---|---|---|
| 1 | 2 | 17 | 2.0 | 0.0 | 3.7 | ND* | insignificant |
| 2 | 2 | 0 | 9.8 | 7.5 | 33.5 | ND | 31 |
| 3 | 3 | 0 | 22.8 | 20.4 | 64.3 | ND | 12 |
| 4 | 3 | 0 | 25.8 | 20.2 | 44.5 | 4.7 | 28 |
| 5 | 3 | 0 | 65.1 | 45.4 | 80.7 | ND | 43 |
| 6 | 3 | 0 | 23.1 | 20.0 | 42.0 | 19.2 | 16 |
|   | 3 | 6 | 7.4 | 5.2 | 10.2 | 53.0 | 42 |
| 7 | 4 | 355 | 10.3 | 3.1 | 18.9 | ND | 23 |
| 8 | 10 | 425 | 25.5 | 18.2 | 39.2 | 15.4 | 40 |

*ND = Not Done due to lack of sufficient lymphocytes
Results are the mean of one experiment performed in triplicate

Example 3

Immunotherapy of Human Ovarian Carcinoma in an Animal Model

In order to investigate the therapeutic effectiveness, MAb-B43.13 was tested in a human-PBL-SCID/BG mouse model. Mice were reconstituted with human-PBL(normal donors) by i.p. injection of 2 to $3 \times 10^7$ PBL/mouse. MAb-B43.13 was administered at 100 μg/mouse in PBS, in different experimental set-ups. An isotype matched control antibody (MOPC21 or MAb-170) and PBS injection served as controls. The ovarian cancer cells NIH: OVCAR-Nu3 were injected i.p. at $1 \times 10^6$ cells/mouse or s.c. at $4 \times 10^6$ cells/mouse. Hu-PBL-SCID/BG mice were either immunized before injection of tumor cells, or after small tumors were established (two weeks after transplantation). In another experiment, tumor-bearing mice (s.c.) were injected with MAb-B43.13 two weeks after tumor transplantation, along with PBL.

Antibody injections were repeated twice in 2-week intervals. Functional and cellular characterization of serum and PBL from these mice demonstrated the successful engraftment of a human immune system in those mice.

All three experiments showed that MAb-B43.13 treatment could: a) delay or prevent development of tumors; b) reduce the size of small, established tumors (s.c. tumor injection) or suppress ascites production; c) delay tumor growth when injected prior to tumor implantation and d) prolonged the survival of mice (i.p. tumor injection).

Human tumor infiltrating lymphocytes (TIL) were identified in mice using flow cytometry, which might contribute to the in vivo anti-tumor activity of MAb-B43.13.

At the endpoints of the therapy study, surviving mice from different treatment groups were euthanized. Blood, spleen, tumor, and peritoneal washes were obtained form the measurement of human immunoglobulin as well as flow cytometric analysis of human PBL in mouse tissues. Tumors were also analyzed by immunohistochemistry.

We first determined whether MAb-B43.13 has in vivo anti-tumor activity, when the tumor was localized within the peritoneal cavity (similar to ovarian cancer patients) and of limited size at start of the treatment. NIH:OVCAR-NU-3 tumor cells (CA125 positive), human PBL, and MAb-B43.13 or control antibody (MAb-170) were all injected intraperitoneally. This treatment regimen maximized the effect of the antibodies on tumor cells. As shown in FIG. 8, MAb-B43.13 antibody had preventive effect on ascites development and significantly prolonged the survival of SCID/BG mice bearing i.p. injected tumor cells (p<0.01, Table 6). The development of ascites production was carefully monitored. Approximately two weeks after detection of ascites, mice became sick and died within a few days. Therefore, mice were terminated as soon as they showed signs of illness and/or discomfort. The percentage of surviving mice was plotted against the time after tumor transplantation. [FIG. 8 legend: ♦, MAb-B43.13+PBL; ■, MAb-170+PBL; ▲, PBS+PBL; ●, tumor only]. The patterns of ascites development in the control groups (MAb-170-PBL, PBS-PBL and no treatment) were found to be similar to each other. The survival times of the mice in these control groups were approximately the same.

TABLE 6

Statistical Analysis of the survival data in MAb-B43.13 treated tumor bearing (i.p.) Human-PBL-SCID/BG mice

| Treatment comparison | mean difference | q | p value |
|---|---|---|---|
| No treatment vs. PBS-PBL | −4.1667 | 0.6411 | >0.05 (NS) |
| No treatment vs. control MAb-PBL | −9.2333 | 1.4207 | >0.05 (NS) |
| No treatment vs. MAb-B43.13-PBL | −35.4 | 5.4468 | <0.01 (S) |
| PBS-PBL vs. control MAb-PBL | −5.0067 | 0.7796 | >0.05 (NS) |
| PBS-PBL vs. MAb-B43.13-PBL | −31.233 | 4.8057 | <0.05 (S) |
| control MAb-PBL vs. MAb-B43.13-PBL | −26.167 | 4.0261 | <0.05 (S) |

The therapeutic studies described above demonstrated that B43.13 antibody could delay or prevent the development of non-established, presumably dispersed tumor cells intraperitonealy. In order to determine whether MAb-B43.13 has also anti-tumor activity on established tumors, NIH:OVCAR-NU-3 tumor cells were injected s.c. into the flank of SCID/BG mice ($4 \times 10^6$ cells/mouse) and allowed to grow before start of the immunizations. Approximately one week after tumor cell inoculation, the mice developed palpable tumors. Mice were divided into four groups and underwent different treatments: MAb-B43.13-PBL, MAb-B43.13 alone. MOPC21-PBL and MOPC21 alone. Treatment of tumor-bearing mice with MAb-B43.13 significantly decreased the tumor growth compared to the control groups as evaluated by tumor size measurement (p<0.05). The inhibition of tumor growth rate as measured by tumor size corresponded to that measured by tumor weight. These results indicate that MAb-B43.13 treatment is also efficacious in mice with established tumors (FIG. 9).

A human immune system was first established in SCID/BG mice by intraperitoneal injection of human PBL. One day later, half of the PBL-reconstituted mice received MAb-B43.13 and the other half was administered with MAb-170 (i.p. immunizations). One week after PBL reconstitution, all of the mice were injected s.c. with NIH:OVCAR-NU-3 tumor cells. An additional control group of mice received s.c. tumor cell injection without prior administration of PBL or antibody. FIG. 10 shows the tumor appearance in mice injected with $2 \times 10^6$ tumor cells for various treatment groups. A consistent delay of tumor appearance in MAb-B43.13-PBL group was observed as compared to both control groups. Tumor establishment of 100% was delayed by nine days in both MAb-B43.13-PBL and MAb-170-PBL groups. Since the tumor take in all groups eventually was 100%, the mean tumor size of the different treatment groups over a period of 2 months was measured and compared. Although the mice in the MAb-170-PBL group also showed delay of tumor appearance compared to the group with no treatment, no significant difference in tumor size was observed between these two groups over the experimental period of two months (FIG. 11). On the other hand, significantly smaller tumors were found in the MAb-B43.13-PBL group at all times (p<0.01) (FIG. 11).

Example 5

Induction of Idiotypic Network to Anti-MUC-1 Antibody in Breast Cancer

MUC-1 proteins (polymorphic epithelial mucin) expressed on malignant epithelium are underglycosylated, which leads to exposure of novel T and B cell epitopes. An anti-MUC-1 murine clone. AR20.5 was generated by immunization of mice with CA15.3 antigen, a glycoprotein consisting of an MUC-1 protein carbohydrate and characterized for its binding specificity to CA15.3 and MUC-1 tandem repeated core peptide by ELISA and to MUC-1 transfectoma by FACS analysis. Injection of MAb-AR20.5 (Ab1) conjugated to KLH into mice carrying MUC-1 transfectoma resulted in anti-idiotypic antibody (Ab2) (FIG. 12) and anti-anti-idiotypic antibody (Ab3) production FIG. 13). A minimum of four injections at a dose of 50 μg/mouse was needed to obtain the measurable humoral response. The Ab2 and Ab3 levels reached their peak after six injections. The anti-idiotypic antibody (Ab2) competed with the native antigen, CA15.3. T-cells proliferation studies showed specific response to the injected antibody and CA15.3 indicating the presence of idiotype specific T-cells (T2) and anti-idiotype specific T cells (T3). See FIG. 14. These results encourage us to use such antibodies for immunotherapy of cancer by generating surrogate antigen via Ab1 injections.

In addition, a breast tumor model was developed using a human MUC-1 gene transfected mouse mammary carcinoma, 413BCR. Groups of mice were treated with Ar 20.5-KLH or human immunoglobulin conjugate, and compared to appropriate positive control (liposomal MUC-1) and negative control (murine immunoglobulin). Immunizations were performed twice before or after tumor implantation at weekly intervals. The tumor volumes were measured weekly and the growth rates assessed. A significant tumor reduction was observed in mice treated with AR 20.5-IgG conjugate compared to other groups. See FIG. 15.

Example 6

A composition according to the invention was produced against CA 19.9 (SLe$^a$), an excellent marker for pancreatic cancer (87%), gastric cancer (68%), and colo-rectal cancer (50%).

The binding agent was AR 44.6, an IgG3 antibody that binds strongly to CA 19.9, and has been shown to mediate tumor killing through CDC in vitro.

Approximately $10^4$ chromium labeled SW 1116 (2200 CPM) were incubated with different concentrations of AR44.6, AR44.4, NS1116, AR18.4, and unspecific mIgG3 (20 μg/mL to 0.0025 μg/mL). The antibodies were incubated for 45 minutes at 4° C. In the treatment groups incubated with HAMA, the antibodies were washed twice with medium and incubated with 1 μg/mL of HAMA for 45 minutes at 4° C. All plates were washed and effector cells (fresh collected human PBLs) or fresh human serum (20% in medium) were added and incubated for four hours. The cytotoxic index (C.I.) was then calculated. Paired T test was used to analyze each concentration.

FIG. 16 shows the results obtained for AR 44.6, AR 44.4, and unspecific IgG3 mediated CDC (with or without human anti-mouse antibodies, HAMA). FIG. 16 shows that AR 44.6 and AR 44.4 are extremely effective in complement-mediated cytotoxicity. Such cytotoxicity is increased in the presence of HAMA. The anti-tumor effect of AR 44.6 was also analyzed in SCID/BG mice reconstituted with human PBL. FIG. 17 shows a reduction in tumor volume as a result of the binding agent and the binding agent/antigen complex.

Example 7

PSA Directed Immunotherapy of Prostate Cancer (Production of AR47.47)

Prostate specific antigen (PSA) represents an attractive target for the immunotherapy of prostate cancer. This glycoprotein is almost exclusively synthesized by the prostatic gland and is currently used for the diagnosis and monitoring of prostate cancer patients. However, since PSA is recognized as a self-antigen, it is essential for effective immunotherapy to develop innovative strategies capable to trigger the immune system and induce a protective, immunity against PSA expressing cells. This example demonstrates the use of an antibody to elicit an anti-idiotype cascade associated with an antigen specific anti-tumor immune response. A large panel of anti-PSA monoclonal antibodies have been produced in our laboratory and these antibodies were evaluated for their potential therapeutic efficacy against prostate cancer. We have demonstrated that the immunization of mice with a selected anti-PSA antibody can induce a specific immunity against PSA itself. These results therefore emphasize the potential use of anti-PSA antibodies for the immunotherapy of prostate cancer.

Hybridoma clones secreting anti-PSA antibodies were produced by fusion of the murine myeloma cells Sp2/O with the splenocytes of a Balb/c mouse immunized with human PSA. An exemplary clone, AR47.47, binds to an epitope of PSA corresponding to amino acid sequences 139-163 of the PSA molecule (see FIG. 18).

The first criteria of selection used to identify the anti-PSA antibody was the ability of this antibody to interact with circulating PSA. Circulating PSA is found either in a free form or complexed to anti-proteases such as α-anti-chymotrypsin and α2-macroglobulin. To screen for clones we used three different forms of PSA: free PSA; PSA complexed to α-anti-chymotrypsin (ISA-ACT); and free PSA non complexing to α-anti-chymotrypsin (PSA-nc). Free PSA corresponds to PSA directly purified from human seminal fluid. Co-incubating free PSA with purified ACT results in the formation of PSA-ACT and PSA-nc. PSA-nc can be separated by gel filtration chromatography. It is believed that PSA-nc may represent the free form of PSA present in the circulation. Complexing of PSA with α2-macroglobulin results in the total encapsulation of PSA. As a consequence, this form of PSA is no longer detectable by monoclonal anti-PSA antibodies. We therefore did not use this form of circulating PSA for the screening.

PSA belongs to the kallikrein family and a high degree of structural homology is found between PSA and the kallikreins HK1 and HK2. The absence of cross reactivity of the anti-PSA antibody with kallikrein isolated from human plasma was used as second criteria for selection.

The hybridoma clone AR47.47 responded to the criteria described above, a strong immunoreactivity was observed with the three forms of PSA used for the screening whereas no cross reactivity was observed with human plasmatic kallikrein. The hybridoma clone AR47.47 was cloned twice by limiting dilution and the second generation clone AR47.47R6R6 was chosen for further studies. Clone AR47.47R6R6 was adapted to standard medium (RPMI 10% FBS) and a cell bank was formed. The absence of mycoplasma contamination was verified by using the Boehringer Manheim mycoplasma test. Clone AR47.47R6R6 has been deposited in the American Type Culture Collection, and has received Accession No. H-B 12526.

We have studied in DBA mice whether the immunization with a binding composition according to the invention (AR47.47) can result in the induction of a specific PSA immunity via the idiotypic network (i.e. induction of Ab3 antibodies). Anti-PSA antibodies (Ab3) could be detected in the serum of animals immunized with AR 47.47, a minimum of two injections of AR 47.47 was required for Ab3 production. No reactivity towards PSA was detected for the control groups (mice immunized with an isotype matched control antibody not related to PSA and mice receiving PBS injections).

AR 47.47 is directed towards a PSA epitope comprised between the sequence 139-163 of the PSA molecule. The anti-PSA antibodies produced by AR 47.47 immunized mice can specifically interact with the PSA peptide 139-163. We can therefore conclude that at least part of the Ab3 produced are identical in term of specificity to AR 47.47. These results demonstrate that the immunization with AR 47.47 can induce a specific anti-PSA immunity in the host (FIG. 18).

Example 8

Anti-Idiotypic Induction of PSA Immunity in Mice

We have studied in mice whether the immunization with anti-PSA antibodies can induce a specific immunity against PSA via activation of the idiotypic network. The goal of this experiment was to demonstrate that the immunization of mice with anti-PSA antibodies (Ab1) can stimulate the immune system to generate anti-idiotypic antibodies (Ab2=surrogate antigen), and anti- anti-idiotypic antibodies (Ab3) capable of reacting with the original antigen.

We used for these experiments a commercially available antibody as a model anti-PSA antibody (RLSD09; ATCC HB-8525). The purified antibody was conjugated to Keyhole Limpet Hemocyanin (KLH) to enhance its immunogenicity. The anti-PSA antibodies conjugated to KLH were still capable of binding to PSA, indicating that the idiotype of the antibodies were not masked by the conjugation procedure. B43.13 antibody, a mouse monoclonal antibody of the same isotype as the PSA antibody (IgG1) was used as the control. B43.13 antibody is specifically directed against the CA125 ovarian tumor antigen and does not cross react with PSA. In addition we verified by FACS analysis that the B43.13 antibody does not bind at the cell surface of Line-1-PSA or P81 5-PSA.

Mice were subdivided into three groups of five mice each. The first group of mice was immunized with anti-PSA antibody conjugated to KLH. The second group of mice was immunized with the control B43.13 antibody conjugated to KLH. The third group of mice received PBS injection. Injections were performed i.p. at 10 days intervals with complete Freund adjuvant for the first injection and incomplete Freund adjuvant for the second injection.

Ab2 is a surrogate antigen capable of mimicking the PSA epitope recognized by the injected anti-PSA antibody. A competitive inhibition assay was established to measure the serum level of Ab2. This assay was performed 5 days after the second injection. An inhibition was observed after incubation in the presence of mouse sera from mice immunized with anti-PSA antibody, but not when sera from mice immunized with control antibody or PBS were used. These results indicate that the immunization of Balb/c mice and DBA mice with the anti-PSA antibody can induce the formation of anti-idiotypic antibody (Ab2) capable of mimicking PSA.

Example 9

Effect of Anti-PSA Immunization on Tumor Development

We have studied in Balb/c mice whether the immunization with anti-PSA antibodies can protect the animals against a subsequent tumor challenge. Balb/c mice were divided into 3 groups of 5 mice each. The first group was immunized with anti-PSA antibody RLSD09 conjugated to KLH, the second group was immunized with control antibody B43 conjugated with KLH, the third group received PBS injections. A total of 4 injections were given for each group using 50 µg of antibodies for each injection. The tumor cells Line-1-PSA were injected intravenously between the third and fourth injections. Nineteen days after tumor inoculation, the mice were sacrificed, the number of tumor foci in the lungs and AB3 levels in the serum were determined.

The tumor burden in the group of mice immunized with anti-PSA mAb was considerably lower compared to the group of mice immunized with control antibody. Of particular interest is the demonstration, in the group of mice immunized with anti-PSA mAb, of a negative correlation between Ab3 levels and the number of tumor foci in the lungs.

Example 10

Anti-Inflammatory Composition

To test for the effectiveness of a composition containing a binding agent in treating inflammation, a double blind experiment was performed on 18 Spraque Dawley rats (weight about 450 g) divided into 3 groups (8 rats in each group).

The first group was vaccinated with KLH conjugated IgM antibody specific for a carbohydrate ligand on leukocytes (250 µg/rat, i.p.). The second group was vaccinated with KLH conjugated IgM antibody with no binding to the same ligand (250 µg/rat, i.p.). The third group was a control group, and received no vaccination.

Inflammation was induced by injecting 1% carrageenan in 0.9% NaCL (type IV), in the rat right hind paw (0.5 ml/rat). Observation of paw edema by water displacement measurement and caliper measurement.

The inhibitory effect of AR18.4 antibody on inflammation was clinically different from the control group and control IgM antibody group.

The results of these experiments are shown graphically in FIG. 19.

Example 11

Photoactivation Increases Immunogenicity

Normal, healthy, Sprague-Dawley rats were used. Animals were randomly grouped (4 per group) to receive four different doses (5 µg, 10 µg, 25 µg and 50 µg) of MAb 43.13. Pre-injection blood samples were drawn prior to initiation of the injection schedule. Each rat received the appropriate dose of MAb diluted in sterile 0.01 M phosphate buffered saline intravenously. A second study group received 20 μg of each MAb preparation with or without Incomplete Freund's Adjuvant (IFA). Blood samples were taken just prior to the dose injection at 0, 21, 42, 63 and 77 days.

MAb-B43.13 is a murine IgG, reactive with CA 125. Antibody preparations consisted of MAb-B43.13 in the native form or in a UV-exposed form (e.g., photoactivated). Native MAb was diluted from a stock concentration of 5 mg/mL with 0.01 M phosphate buffered saline to doses of 5, 10, 25 and 50 μg/100 μL. UV exposed MAb was reconstituted from the lyophilized form with 0.01 M phosphate buffered saline (2.2 mg/0.47 mL) and diluted to obtain the same doses as for the native MAb.

An assay was developed to measure the rat anti-mouse response in the serum of the injected animals. Anti-isotype rat anti-mouse antibodies were measured using an ELISA plate coated with an isotype matched control antibody, MOPC 21. Samples were diluted $\frac{1}{100}$, allowed to react with the coated antibody, washed, and bound antibody detected using peroxidase conjugated goat anti-rat IgG (H+L) with ABS substrate. Unknowns were read off a standard curve generated using a commercial rat anti-mouse antibody.

The results of the rat anti-mouse (RTAMA) analysis of sera from the various groups of rats injected with native and UV exposed MAb-B43.13 is shown in Table 7 and Table 8. The immunological response to the preparations is expressed in terms of the number of responders in each group, with the numerical cut-off defined in the tables. This value (mean of all pre-injection samples (blanks)+3 S.D.) ensures that a true positive response is measured and the results are unlikely to be due to assay variation. The tabulation of responders is probably more meaningful given that the fluctuation of the magnitude of response can be very large and therefore, hinder interpretation.

TABLE 7

ANIMAL RESPONSE* TO INTRAVENOUS INJECTION OF NATIVE AND UV EXPOSED MAb-B43.13 PREPARATIONS

| Sampling | | Number of Responders | | | |
|---|---|---|---|---|---|
| Time | Preparation | 5 μg | 10 μg | 25 μg | 50 μg |
| Pre-injection (blank) | Native | NA** | NA | NA | NA |
| | UV exposed | NA | NA | NA | NA |
| Day 21 | Native | 0 | 0 | 0 | 0 |
| | UV exposed | 2 | 3 | 1 | 1 |
| Day 42 | Native | 0 | 1 | 0 | 1 |
| | UV exposed | 2 | 3 | 4 | 3 |
| Day 63 | Native | 1 | 3 | 3 | 3 |
| | UV exposed | 2 | 4 | 3 | 4 |
| Day 77 | Native | 2 | 2 | 2 | 1 |
| | UV exposed | 3 | 4 | 4 | 4 |

*Number of animals responding in a group of four (RTAMA values ≧ pre-injection sample mean + 3 S.D.)
**NA = Not Applicable The data tends to confirm that the response to the UV exposed MAb-B43.13 occurs earlier (after only one injection) as shown by the greater number of responders at all dose levels in the Day 21 groups.

Furthermore, at all other time periods (and after multiple injections), the proportional response of each group given intravenous UV exposed MAb-B43.13 is greater. It may be suggested that the response is sustained longer for UV exposed MAb-B43.13 since the native MAb-B43.13 appears to show a reduced response rate from Day 23 to Day 77. Actual values of increased response at day 77 are shown in Table 8.

TABLE 8

TOTAL AND $AB_2$ INDUCTION IN RATS INJECTED WITH NATIVE OR UV-EXPOSED MAB--B43.13

| | TOTAL IMMUNE RESPONSE (mean ± S-E) | $Ab_2$ RESPONSE (mean ± S-E) |
|---|---|---|
| Native Mab - B43.13 | 38.47 ± 2.99* | 18.77 ± 8.23 |
| UV-exposed Mab - B43.13 | 1608.67 ± 369.39* | 87.27 ± 45.11 | n = 3
*p = 0.0496

Example 12

Protein Modification as a Result of UV Exposure

The final chemical species present after photoactivation are specific for a given set of exposure conditions and the composition of the matrix solution (as described above). For simple polypeptides containing any of the three primary, UV absorbing (UV-B) amino acids (cystine, tryptophan, tyrosine) the consequences of UV exposure can lead to amide bond cleavage, disulfide bond cleavage, alteration of absorbing amino acids and alteration of adjacent or close proximity amino acids. These changes are brought about by direct photoionization or photoexcitation and indirectly by radical formation from other constituents. The nature and extent of these modifications is highly dependent on the chemical reactivities of the species generated and other constituents reactive tendencies or stabilizing/quenching capabilities. For this size of molecule any alteration generally results in dramatic changes in biological function.

These same reactions can take place in larger proteins, however secondary and tertiary structural elements present differing substrates for UV exposure in spite of similar amino acid sequences. Therefore, the hydrophobic/hydrophilic nature and proximal amino acids from distant chain sequences as a result of folding alter the micro-environment and therefore influence the degree and nature of the modification, in addition to other constituents issues stated above. Given the predominance of the tryptophan absorption profile in this UV band width, it is thought to be the primary site of the initial photoactivation process, but direct action on cysteine and tyrosine are also viable.

The mechanism for indirect amino acid modifications has been proposed as local hydrated electron generation or direct energy transfer from the primary absorbing site. The primary observed changes for large proteins focus on measurable chemical/biochemical changes such as absorption and fluorescence determinations of aromatic amino acids which relate to global modifications. Individual amino acid alterations be detected in this group of proteins where sulfhydryl content can be determined as evidence of cysteine disulfide cleavage and/or where a critical amino acid for function is involved. For smaller proteins amino acid hydrolysis and complete quantitation can be performed. The primary concern for functional large proteins, such as enzymes, receptor, or antibodies, is therefore not specific amino acid modification but the consequences of any change on their biological function, and has invariably been described as loss of enzyme function, receptor recognition, or antigen binding.

Example 13

UV Exposed B43-13/CA125 Antibody/Antigen Complex Produces Better CA125 Specific Cellular Immune Response and Better Humoral Response Better cellular immune response was observed when the UV exposed antibody was presented in association with the antigen to T-cells. Thus, macrophages isolated from mouse peritoneal cavities were stimulated with native B43.13 or UV exposed B43.13 in association with CA125 and presented to CA125 specific mouse T-cells isolated from mice injected with CA125. Control experiments included stimulation of the macrophages without the antigen. When the proliferation of T-cells as monitored by [$^3$H]—thymidine uptake was followed, optimal stimulation index was observed in macrophages stimulated with UV exposed B43.13-CA125 complex. The results are summarized in Table 9 below.

TABLE 9

| STIMULATING AGENT[1] | STIMULATION INDEX[2] |
|---|---|
| CA125 | 2.76 |
| Native MAb - B43.13 | 3.98 |
| UV-exposed MAb - B43.13 | 3.31 |
| Native MAb - B43.13 - CA125 | 4.71 |
| UV-exposed MAb - B43.13 - CA125 | 5.28 |

[1]1 µg/ml of the antibody and 100 Units/ml CA125 were used.
[2]Mean of three individual experiments done in triplicate.

Example 14

Immunophotodynamic Therapy

An immune competent mouse model is available for the MUC-1 system. The MUC-1 transfectant 413 BCR forms tumors (subcutaneous or intravenous) in BALB/c or CB6F1 mice. The BALB/c animal model was used to test HBBA-R2-SL, HBBA-R2 SIL with AR20.5 and B43.13 (SL=stealth liposome; SIL=stealth immunoliposome). The model has the advantage that the bystander effect of the immune system can be analyzed. Help from the immune system, especially from macrophages, has been reported to augment the immune system for the outcome of PDT and as necessary for obtaining complete response rates. BALB/c mice for injected with 2–2.5×10$^6$ 413BCR cells into the right flank (s.c.).

Tumors appeared after 7-10 days. When tumors reached a diameter of about 5 mm, hypocrellin formulations were injected iv. at 1 mg/kg. Two hours post injection of HBBA-R2, light treatment was performed as described for HBEA-R1 at 40 J/cm$^2$ (>600 nm). Mice were followed by measuring tumor size. When tumor size reached 4-times pretreatment volume, mice were sacrificed. Tumors were followed for 2 months and survival curves were calculated, plotted and compared to the light-only treatment group.

For stealth immunoliposome compositions, two different antibodies were used: AR20.5, which binds to 413BCR cells, and B43.13 as a negative control. Tumors were measured every second day in three dimensions. When tumors reached 4 times pre-treatment volume, mice were sacrificed. Mice treated with light only or drug only were used as control.

Immunoliposomes with AR20.5 showed complete cure in the presence of light (FIG. 20). The non-specific immunoliposomes, coupled with B43.13 show therapeutic efficacy comparable to SL. The HBBA-R2-SIL [AR20.5] also showed improved survival in the dark, compared to mice treated with light only or HBBA-SIL[B43.13] plus light. These results suggest a therapeutic effect of AR20.5 in this model and underline the importance of combined therapy using PDT and antibody vaccine.

For all formulations tested, immunoliposomes specific for the tumor showed the best therapeutic effect. This was also reflected when tumor volumes were used for comparison. The reason for the enormous differences between SL and SIL is not yet completely understood. The data suggest that immunoliposomes might cause an immune response in BALB/c mice that can help killing the tumor. From the biodistribution data we know that HBBA-R2 uptake at the tumor is slightly higher with SIL compared to SL.

Example 15

The goal of this study was to construct a fusion protein of scFv linked to biotin mimetic sequence (BMS), and express in the *P. pastoris* expression/secretion system by using cancer-therapeutic monoclonal antibody MAb B43.13 which selectively recognizes a unique epitope of CA125 expressed on ovarian carcinomas. The use of scFv is advantageous in CA125 assays for the serum samples, from which patients were treated with a MAb B43.13-based vaccine, even in presence of HAMA. Two constructs of scFv derivatives with additional C-terminal extensions containing c-myc/BMS (pDL-5), and spacer/BMS (pDL-9), were designed. The scFv without BMS sequence was used as a negative control molecule in biotin/streptavidin assays.

It has been generally believed that the recombinant proteins expressed and secreted from the recombinant *P. pastoris* cells retains their biological activities. In order to demonstrate that the scFv proteins have their intrinsic binding activities, competitive radioimmunoassay (RIA) experiments were carried out. We found that the purified scFv samples isolated from pDL-5 and pDL-9-transformed cells showed positive binding activity in RIA, in comparison with the control scFv and their parental MAb B43.13.

The design of biotin mimetic sequence was based upon the results obtained from screening of cyclic peptide phage libraries to identify the ligand that bound Streptavidin with high affinity. The biotin-Streptavidin interaction is widely used in immunoassays to enhance the detection signal. To demonstrate that the fusion proteins exhibit biotin mimetic conformation and to compare the biotin detection between these two constructs (pDL-5 and pDL-9), the ELISA experiments with direct CA125 binding and "sandwich" CA125 binding were carried out. One of the reasons might be that linear epitope sequence of c-myc represented a rigid structural conformation between the scFv and BMS motif. Therefore, it may disturb the loop structure of BMS or the binding of BMS to Streptavidin.

Example 16

Three derivatives of scFv with additional C-terminal extensions containing mouse and human tuftsin (pDL-6 and pDL-11), or a control sequence (pDL-10), were designed. To construct plasmids pDL-6, pDL-10, and pDL-11, DNA oligodeoxyribonucleotides (5'-GAATTCTGGAGGTGGTACCCAGCCTAGGTAGC-3', 5'-GAATTCAGCTGGAGGTGGTGGATGTGC-3' and

5'-GAATTCTGGAGGTGGTACCAAGCCTAGGTAGC-3)

coding for the amino acid sequences N-SerGlyGlyGlyThrGlnProArg-C,

N-SerAlaGlyGlyGlyGlyCysAla-C, and N-SerGlyGlyGlyThrLysProArg-C, were used by inserting fragments in EcoRI and EagI sites of pPIC-B43. The plasmid DNAs were transformed into competent GS115 cells by electroporation and the resulting transformants were selected on histidine-deficient media. All positive clones obtained were isolated, cultured in induction media, and analyzed for protein expression in SD S-PAGE followed by Commassie staining. The scFv-tuftsin proteins were produced in minimal media to simplify some downstream protein purification process.

In order to evaluate the anti-idiotypic response, six to 8-week-old BALB/c mice were immunized with 50 μg scFv-tuftsin subcutaneously (Day 0). Two weeks later the mice were received 25 μg of scFv-tuftsin intraperitonealy. The serum of mice was collected on Day 7, 14 and 21.

The anti-idiotypic antibody production were detected by enzyme-linked immunosorbent assay (ELISA). Briefly, chimeric B43.13 were coated to a solid surface and then blocked by 3% BSA/PBS. The chimeric B43.13 were incubated with serum samples for 1 h and then incubated with goat anti-mouse H+L-HRPO for another hour followed three times wash with Tween 20/PBS. A color reaction was developed by adding 50 μl of substrate solution. Absorbence was read at 405 nm. The same procedure was applied to detect anti-anti-idiotypic antibody (Ab3) production except CA125 was coated to ELISA plate at the beginning.

The data shows that it is possible to detect both Ab2 and Ab3 in the serum samples and this indicates that scFv-tuftsin retained the idiotypic immunogenicity which could trigger humoral immune response in mice. We found that the mice immunized with scFv-tuftsin started to show strong anti-idiotypic antibody (Ab2) production after day 20 post the first immunization. However, the anti-anti-idiotypic antibody (Ab3) production appeared earlier, peaking around day 15. This indicates that induction of an idiotypic network response might be an important effector mechanism in MAb-based therapy.

Example 17

The murine monoclonal antibody AR18.4 is a candidate for the development of an anti-gastrointestinal cancer compound. MAb-AR 18.4 binds to tumor antigen CA19.9, a Sialyl Lewis$^a$ antigen which is now generally recognized as one of the most important tumor-associated markers for gastrointestinal cancer. An approach of chimerization of antibody is to construct mouse-human antibody, which is composed of mouse variable region and human constant region, by using recombinant DNA technology. Most reports demonstrate the chimeric antibody is able to retain the same specific binding activity to the antigen as its parental mouse antibody, but avoid the human anti-mouse antibody (HAMA) response with in vivo applications.

Experimental Strategies:

cDNA isolation of V-genes: RT-PCR experiments were carried out to isolate antibody variable genes using specific primers. The cDNAs were then cloned into cloning vector pBluscript for DNA sequencing.

Chimeric Antibody Construction: chimeric clones of PAH-18.4H8PCRII#8 and PAG-18.4L20PCRII#19 was obtained by ligating PAG4622-18.4LPCRII and PAH46.6-18.4HPCRII as expression vectors and inserts were obtained from PBKS-18.4L20PCRI#14 and PBKS-18.4HPCRII #19. Chimeric clones were used for transfection of SP2/0 cells. To obtain the most efficient method for co-transfection of these cells control plasmid pSV-β gal DNA was used as a positive control plasmid to obtain the optimal conditions for transfection into cells.

Transfection: both methods of transfection showed successful transfection efficiency. Lipofectamine causes some cell death but most cells (80%) of cells that stay alive are transfected. In electroporations method cells transfection efficiency was high and cells that were transfected were growing into colonies which contained the new control plasmid. After establishing optimal conditions for transfection of SP2/0 cells co-transfection of SP2/0 cells with PAH-18.4 and PAG-18.4 was done.

Lipofectamine method: 2 ug of each DNA plasmid was used. The same protocol was mentioned above was followed. 24 hours after transfection, cells were harvested from 6-well plates and cells were seeded in 96-well plates with cell density of $1.0 \times 10^4$ cells/well. After overnight incubation at 37° C., selection media was added to each well in 1:1 ratio. Selection media includes 1 μg/μl of mycophenolic acid and 5 mM histodinal, 7.5 PH which was adjusted using NaOH. Selection media was changed every 3 days and cells were in selection media for 12 days.

Electroporation method: 20 μg of each DNA plasmid was used. The same method as mentioned above was used for transfection. Cells were plated into 96-well plates after electroporation with $1 \times 10^4$ cells/well density. 24 hours after transfection selection media was added to cells. Cells were kept under selection media for 12 days and media was changed every 3 days.

To determine whether transfection has occurred supernatant of transfected cells were used for ELISA to assay the production of desired chimeric protein. CAl 9.9 was used to coat the plates and they were blocked by 3% BSA. For primary antibody tissue culture supernatant was used and for secondary antibody rabbit anti human (Fab'2) IgG (H+L) was used. Assay from ELISA gave positive results for production of desired product.

Example 18

Construction and Characterization of Single Chain Antibody

The MAb B43.13 variable domain sequences were PCR-amplified using sequence specific primers, and engineered into a cloning vector with scFv orientation of V1-linker-Vh. The DNA fragment coding for the scFv was then subcloned into *P. pastoris* vector, pPIC-9 with aF secretion signals, resulting in recombinant plasmid pPIC-B43.13. One derivative of pPIC-B43.13 with additional C-terminal extensions containing one cysteine (pDL10) was designed to form a disulfide bridge. Therefore, the antigen binding activity can be enhanced by increase of avidity. To construct plasmids pDL10, DNA oligodeoxyribonucleotides (5'-GAAT-TCAGCTGGAGGTGGTGGATGTGC-3') coding for the amino acid sequences, N-SerAlaGlyGlyGlyGlyCysAla-C were used by inserting fragments in EcoRI and EagI sites of pPIC-B43.13.

The plasmid DNAs were transformed into competent GS115 cells by electroporation and the resulting transformants were selected on histidine-deficient media. After screening for integration at the correct loci, (i.e. colonies can grow on a –his/+glycerol plate but grow slowly on a –his/+methanol plate), all positive clones obtained were isolated, cultured in induction media, and analyzed for protein expression in SDS-PAGE followed by Coomassie staining, as we described previously (Luo et al., 1997). The protein samples were dialysed against PBS and concentrated using Centricon 10 filter (Amicon, Danvers, Mass.).

Purity of scFv-pDL10 were analyzed by SDS-PAGE under reducing condition. CA125-binding specificity was determined using a ELISA in which microtiter plate wells were coated with CA125, CA15.3 (a human breast cancer antigen), or CA19.9 (a human colon cancer antigen). The bound single chain antibody was detected by peroxidase-labeled goat ant-mouse H and L (Southern Bio. Associ.) For 1 hour at room temperature. Following three washes, 50 µl of ABTS substrate solution was added. The absorbance was measured at 405 nm.

Single chain Fv containing poly(lactic-co-glycolic acid) microspheres were prepared by a double-emulsion technique with some modifications (Uchida et al., 1994). $Na^{125}I$ labeled scFv-pDL10 was used as a tracer to determine the loading efficiency. Briefly, scFv-pDL10 (1.5 mg) and $Na^{125}I$-scFv-pDL10 (0.4 µg) in PBS was mixed with 500 µl of chloroform containing 100 mg PLGA 50/50 (Lactel). The mixture was sonicated for 15 s using a sonicator homogenizer (Heat System, New York). The resulting emulsion was added to 2 ml of 9% poly(vinyl alcohol) (PVA, Aldrich, USA). Emulsification was continued by sonicate on for 1 min. The emulsion was transferred to 8 ml of 9% PVA and stirred for 2 hours for evaporation of the chloroform. Microspheres were recovered by centrifugation (15 min, 15000 rpm) and have washed with distilled water and freeze dried for at least 24 hours.

BALB/c female mice 6-8 weeks of age were used in all in vivo experiments. The immunization groups included five groups: 1) immunized with PLGA microspheres, 2) immunized with scFv-pDL10, 3) immunized with scFv-pDL10 formulated in PLGA microspheres, and the other two groups immunized with the mixture of formulated scFv-pDL10 and GM-CSF or TNF-α. After collection of preimmune serum samples, groups of 4 mice received two subcutaneous immunizations on day 0 and day 14, followed by two intraperitoneal immunizations on day 21 and day 28. The dose for immunization was 10 mg of the microspheres for s.c., 5 mg for i.p. For other groups received no microspheres, the dose of scFv-pDL10 matched the amount formulated. The cytokines were purchased from Southern Bio. Associ. (USA) and were given to mice at a dose of 0.1 µg per day. Tail vein blood samples were taken periodically into Microtainer tubes (Becton Dickinson, USA) and frozen at −80° C. until assay.

Example 19

Dose

Those with skill in the art recognize that the administered dosage can vary widely based on a wide set of different circumstances. The following provides preliminary dosage guidelines.

Retrospective analysis of more than 100 patients who have been injected up to ten times with a 2 mg dose of MAb-B43.13 indicated that some of these patients experienced: a) an unusual course of their disease, characterized by unexpectedly long survival times; and b) no significant adverse reaction or toxicity.

Immunological studies were conducted to understand and evaluate the in vivo mechanism of action of MAb-B43.13. These studies indicated that the extent of anti-idiotypic induction in patients injected with a 2 mg dose of MAb-B43.13 was unrelated to the number of injections or the clinical stage of their disease. However, anti-idiotypic induction is dependent on the levels of the circulating CA 125 present in the patient's sera. Additional experiments demonstrated that the injection of MAb-B43.13 into patients with measurable serum CA 125 led to the formation of antigen-antibody complexes, resulting in antigen epitope presentation and antigen-specific humoral and cellular response to the tumor.

These studies indicate that an effective dose requires only enough antibody to optimally deliver and present all possible circulating CA 125 antigen to the 3 immune system. In vitro studies indicated that 1 ng of MAb-B43.13 can bind 10 units of CA 125. Assuming 40 mL of plasma per kg of body weight, the injection of 2 mg of MAb-B43.13 into a 60 kg patient can bind approximately 8333 U/mL of CA 125 in serum. Since all of the ovarian cancer patients tested to date have had far less than 8333 U/mL of CA 125 in their serum, an injection of 2 mg of MAb-B43.13 is more than sufficient to induce the required immune response. Additionally, in patients that received radiolabeled MAB-B43.13 for immunoscintographic confirmation of the disease, the results of imaging were excellent in spite of high serum CA 125, suggesting that there is excess MAB-B43.13 for specific tumor uptake.

Furthermore, multiple injections at selected intervals appear to provide optimal benefits to patients, since CA 125 is generated throughout the course of the disease.

Finally, the retrospective analysis showed that the 2 mg dose appears to have therapeutic efficacy; none of the patients (>100) have developed any serious side effects or adverse reactions. If the total HAMA response is an indication of anti-idiotypic induction, a 2 mg dose generates significant levels of anti-idiotypic antibodies to produce the desired therapeutic benefit. Multiple injections of 2 mg of MAb-B43.13 at selected intervals appears to maintain the anti-idiotypic antibodies at the desired therapeutic level without causing any isotypic HAMA-induced toxicity.

A range of effective doses or a therapeutically acceptable amount of MAb-B43.13 therefore includes, but is not limited to, 2 mg.

While the present invention has been described in some detail by way of illustration and example, it should be understood that the invention is susceptible to various modifications and alternative forms, and is not restricted to the specific embodiments set forth. It should be understood that these specific embodiments are not intended to limit the invention, and the intention is to cover all modifications, equivalents, and alternatives falling within the spirit and scope of the invention.

We claim:

1. A method of treating an oncological disease comprising stimulating a multi-epitopic immune response to a tumor-associated antigen comprising:
    administering to a host a complex formed from a soluble tumor-associated antigen and an antibody or antigen binding fragment thereof that binds to a first epitope of the tumor-associated antigen, wherein the tumor-associated antigen is CA 125, and wherein the administration of the complex induces host antibodies reactive with at least one other epitope of the tumor-associated antigen.

2. The method of claim 1, wherein the antibody is selected from the group consisting of a monoclonal antibody, a single chain antibody, a humanized antibody, and a chimeric antibody.

3. The method of claim 1, wherein the host is a human.

4. The method of claim 1, wherein the complex is administered with an adjuvant.

5. The method of claim 1, wherein the antibody or antigen binding fragment thereof of the complex is formulated at a dose of from about 0.1 µg to about 2 mg per kilogram of body weight of the host.

6. The method of claim 1, wherein the complex induces cytotoxic T cells reactive with the antigen.

7. The method of claim 1, wherein the antibody or antigen binding fragment thereof is formulated in the complex at a dose of about 2 mg per host.

8. The method of claim 1, wherein the antibody or antigen binding fragment thereof is formulated in the complex at a dose of from about 0.1 μg to about 200 μg per kilogram of body weight of the host.

9. The method of claim 1, wherein the antibody is produced by the hybridoma having ATCC deposit number PTA-1883.

10. A method of treating an oncological disease comprising stimulating a multi-epitopic immune response to a tumor-associated antigen comprising administering to a host a complex consisting essentially of a soluble tumor-associated antigen and an antibody or antigen binding fragment thereof that binds to a first epitope of the tumor-associated antigen, wherein said tumor-associated antigen is CA 125, and wherein the administration of the complex induces host antibodies and cytotoxic T cells reactive with the tumor-associated antigen.

11. The method of claim 10, wherein the antibody is produced by the hybridoma having ATCC deposit number PTA-1883.

12. A method of treating an oncological disease comprising stimulating a multi-epitopic immune response to a tumor-associated antigen comprising administering to a host a complex consisting essentially of a soluble tumor-associated antigen and an antibody or antigen binding fragment thereof that binds to a first epitope of the tumor-associated antigen, wherein said tumor-associated antigen is CA 125, and wherein the administration of the complex induces cytotoxic T cells reactive with the tumor-associated antigen.

13. The method of claim 12, wherein the complex further induces host antibodies reactive with at least one other epitope of the tumor-associated antigen.

14. The method of claim 12, wherein the antibody is produced by the hybridoma having ATCC deposit number PTA-1883.

15. A method of treating an oncological disease comprising administering to a host a complex formed from a soluble tumor-associated antigen and an antibody or antigen binding fragment thereof that binds to a first epitope of the tumor-associated antigen, wherein said tumor-associated antigen is CA 125, and wherein the administration of the complex induces host antibodies reactive with at least one other epitope of the tumor-associated antigen.

16. The method of claim 15, wherein the complex induces cytotoxic T cells reactive with the tumor-associated antigen.

17. The method of claim 15, wherein the complex induces host antibodies reactive with at least one other epitope of the antigen.

18. A method of treating an oncological disease comprising administering to a host a complex formed from a soluble tumor-associated antigen and an antibody or antigen binding fragment thereof that binds to a first epitope of the tumor-associated antigen, wherein said tumor-associated antigen is CA 125, and wherein the administration of the complex induces cytotoxic T cells reactive with the tumor-associated antigen.

19. A method of treating an oncological disease comprising stimulating a multi-epitopic immune response to a tumor-associated antigen comprising administering to a host a complex formed from a soluble tumor-associated antigen and an IgG antibody or antigen binding fragment thereof that binds to a first epitope of the tumor-associated antigen, wherein said tumor-associated antigen is CA 125, and wherein the administration of the complex induces host antibodies reactive with at least one other epitope of the tumor-associated antigen.

20. The method of claim 19, wherein the antibody is produced by the hybridoma having ATCC deposit number PTA-1883.

21. A method of treating an oncological disease comprising stimulating a multi-epitopic immune response to a tumor-associated antigen comprising administering to a host a complex formed from a soluble tumor-associated antigen and an IgG antibody or antigen binding fragment thereof that binds to a first epitope of the tumor-associated antigen, wherein said tumor-associated antigen is CA 125, and wherein the administration of the complex induces cytotoxic T cells reactive with the tumor-associated antigen.

22. The method of claim 21, wherein the antibody is produced by the hybridoma having ATCC deposit number PTA-1883.

23. The method of any of claims 1, 10, 12, 15, 18, 19, and 21, wherein the antibody is a non-human antibody.

24. The method of any of claims 1, 10, 12, 15, 18, 19, and 21, wherein said antibody or antigen binding fragment thereof comprises an Fc portion that binds an Fcγ RII receptor.

25. The method of any of claims 1, 10, 12, 15, 18, 19, and 21, wherein said antibody is an IgG1 antibody or an antigen-binding fragment thereof.

26. A method of treating an oncological disease comprising stimulating a multi-epitopic immune response to a tumor-associated antigen comprising: administering to a host a complex formed from a soluble tumor-associated antigen and an antibody or antigen binding fragment thereof that binds to a first epitope of the tumor-associated antigen,
   wherein the tumor-associated antigen is CA 125, and the first epitope of the tumor-associated antigen is the epitope bound by an antibody produced by the hybridoma having ATCC deposit number PTA-1883, and,
   wherein the administration of the complex induces host antibodies reactive with at least one other epitope of the tumor-associated antigen.

27. A composition suitable for administration to a host for altering immunogenicity of a tumor-associated antigen comprising a complex of a soluble tumor-associated antigen and an antibody or antigen binding fragment thereof that specifically binds to an epitope of the antigen, wherein said tumor-associated antigen is CA 125, and wherein administration of the composition to a host results in a multi-epitopic immune response including production of antibodies reactive with at least one other epitope of the tumor-associated antigen.

28. The composition of claim 27, wherein the antibody is selected from the group consisting a monoclonal antibody, a single chain antibody, a humanized antibody, and a chimeric antibody.

29. The composition of claim 27, wherein the antibody is a monoclonal antibody.

30. The composition of claim 27, wherein the host is a human.

31. A composition suitable for administration to a host for altering immunogenicity of a tumor-associated antigen comprising a complex of a soluble tumor-associated antigen and an IgG antibody or antigen binding fragment thereof that specifically binds to an epitope of the antigen, wherein said tumor-associated antigen is CA 125, and wherein administration of the composition to a host results in a multi-epitopic immune response including production of antibodies reactive with at least one other epitope of the tumor-associated antigen.

32. The composition of claim 27 or 31, wherein the antibody is a non-human antibody.

33. The composition of claim 27 or 31, wherein said antibody or antigen binding fragment thereof comprises an Fc portion that binds an Fcγ RII receptor.

34. The composition of claim 27 or 31, wherein said antibody is an IgG1 antibody or an antigen-binding fragment thereof.

35. The composition of claim 27, or 31, wherein the antigen is a human antigen.

36. The composition of claim 31, wherein the antibody is produced by the hybridoma having ATCC deposit number PTA-1883.

37. A composition suitable for administration to a host for altering immunogenicity of a tumor-associated antigen comprising a complex of CA 125 and a monoclonal antibody produced by the hybridoma having ATCC deposit number PTA-1883 or antigen binding fragment thereof that specifically binds to an epitope of CA 125, wherein administration of the composition to a host results in a multi-epitopic immune response including production of antibodies reactive with at least one other epitope of CA 125.

* * * * *